United States Patent
Ji et al.

(10) Patent No.: US 11,096,951 B2
(45) Date of Patent: Aug. 24, 2021

(54) PREBIOTIC COMPOSITION CONTAINING BUTYRYL-FRUCTOOLIGOSACCHARIDES

(71) Applicant: BIFIDO CO., LTD., Gangwon-do (KR)

(72) Inventors: Geun Eog Ji, Seoul (KR); Min Hee Um, Jecheon-si (KR); Si Ni Kang, Seoul (KR); Myeong Soo Park, Gyeonggi-do (KP); Bin Kwon, Gangwon-do (KR)

(73) Assignee: BIFIDO CO., LTD., Hongcheon-Gun (KR)

( * ) Notice: Subject to any disclaimer, the term of this patent is extended or adjusted under 35 U.S.C. 154(b) by 0 days.

(21) Appl. No.: 16/023,834

(22) Filed: Jun. 29, 2018

(65) Prior Publication Data
US 2019/0343857 A1 Nov. 14, 2019

(30) Foreign Application Priority Data
May 8, 2018 (KR) .................. 10-2018-0052402

(51) Int. Cl.
*A61K 31/7024* (2006.01)
*A23L 33/21* (2016.01)

(52) U.S. Cl.
CPC .......... *A61K 31/7024* (2013.01); *A23L 33/21* (2016.08); *A23V 2002/00* (2013.01)

(58) Field of Classification Search
CPC . A61K 31/733; A61K 31/702; A61K 31/7024
See application file for complete search history.

(56) References Cited

U.S. PATENT DOCUMENTS 7,812,004 B2 * 10/2010 Frippiat ............... A61K 31/733 514/54
2008/0213341 A1 * 9/2008 Haji Begli ........... A61K 31/70 424/439

FOREIGN PATENT DOCUMENTS

KR 10-1628769 B1 6/2016
KR 10-1670092 B1 10/2016

OTHER PUBLICATIONS

Madhusha, "Main Difference between Oligosaccharides and Polysaccharides", Pedia.com, available at https://pediaa.com/difference-between-oligosaccharides-and-polysaccharides/; published online Jul. 2017 (Year: 2017).*
Polyviou, T. et al., Alimentary Pharmacology and Therapeutics, "Randomised clinical study: inulin short-chain fatty acid esters for targeted delivery of short-chain fatty acids to the human colon", published online Jul. 2016, vol. 44, pp. 662-672 (Year: 2016).*
Roberfroid, M. B. et al., The Journal of Nutrition, "The Bifidogenic Nature of Chicory Inulin and Its Hydrolysis Products", Jan. 1998, vol. 128, No. 1, pp. 11-19 (Year: 1998).*
Pokusaeva, K. et al., Genes Nutr., "Carbohydrate metabolism in Bifidobacteria", 2011, vol. 6, pp. 285-306 (Year: 2011).*
Stewart, M. et al., Nutrition Research, "Fructooligosaccharides exhibit more rapid fermentation than long-chain inulin in an in vitro fermentation system", 2008, vol. 28, pp. 329-334 (Year: 2008).*
Notification of Reason for Refusal dated Jul. 31, 2019 for related Korean Patent Application No. 10-2018-0052402.
F.R.J. Bornet, et al.; "Nutritional aspects of short-chain fructooligosaccharides: natural occurrence, chemistry, physiology and health implications"; Digest Liver Dis; 2002; 34 (SUPPL 2); pp. S111-S120 (10 pages).

* cited by examiner

*Primary Examiner* — Bahar Craigo
(74) *Attorney, Agent, or Firm* — Sughrue Mion, PLLC

(57) ABSTRACT

Provided is a prebiotic composition containing butyryl-fructooligosaccharide (B-FOS). B-FOS of the present invention facilitates selective growth of probiotics, thereby controlling intestinal microbes and contributing to physiological functions as an energy source of intestinal epithelial cells.

2 Claims, 24 Drawing Sheets

PREBIOTIC COMPOSITION CONTAINING BUTYRYL-FRUCTOOLIGOSACCHARIDES

BACKGROUND OF THE INVENTION

Field of the Invention

The present invention relates to a prebiotic composition containing butyryl-fructooligosaccharides.

Description of the Related Art

A great number and variety of microbes live as colonies in the gastrointestinal tract (GI) and such colonies are called "enteric microbes". They are essential for normal physiology and functions of the gastrointestinal tract because they play an important role in the immune function, digestion and metabolism, while constituting the ecosystem within the intestinal tract. Human intestinal microflora is quite resistant to environmental changes, but factors such as antibiotics, stress, dietary or certain diseases cause changes in intestinal microflora. Such a change in the configurations and functions of enteric microbiota is referred to as "intestinal dysbiosis". The most common definition is the unbalance of beneficial bacteria such as *Bifidobacterium* and *Lactobacillus*, and harmful bacteria such as *Escherichia coli*. This imbalance is known to directly or indirectly relate to various diseases such as autoimmune diseases, inflammatory bowel diseases, obesity and the like.

Probiotics are living microorganisms that have a beneficial function by maintaining the balance of human enteric microbiota. They inhibit the growth of harmful bacteria by reduction in intestinal pH through production of short chain fatty acids (SCFAs) and competition of intestinal nutrients and barrier attachment sites. In addition, they are known to have beneficial functions to the human body such as immune activation and alleviation of lactose intolerance. Representative microbes used as probiotics include Bifidobacteria and lactic acid bacteria (LAB). Lactic acid bacteria produce lactic acid by fermenting carbohydrates, which include the genus of *Lactobacillus, Streptococcus, Leuconostoc* and the like. Meanwhile, *Bifidobacterium* is a bacterium that uses various oligosaccharides as an energy source. In the process of converting hexose to lactic acid or acetic acid, there are unique features that an enzyme called "fructose-6-phosphate phosphoketolase" acts and gas is not generated during the fermentation process.

Prebiotics mean substances that are not digested by humans, and are selectively fermented by intestinal microorganisms and thus regulate their growth and metabolic changes to help the host's health. There among, fructooligosaccharides (FOS) are oligosaccharides with fructose molecules bound to sugar at 13-1,2. It is known that FOS can be fermented by *Lactobacillus* and *Bifidobacterium*, and intake of FOS increases *Bifidobacterium* and *Lactobacillus* species. FOS can increase the number of intestinal probiotic strains, which may be beneficial to humans, but harmful bacteria and non-probiotic strains, which are capable of metabolizing FOS in the intestines, may cause adverse effects. Accordingly, there is urgent need for a solution to this.

PRIOR ART

Patent Document (Patent Document 1) Korean Patent No. 10-1628769 (Jun. 2, 2016) discloses a method for preparing a mixed sugar composition containing fructooligosaccharides.

(Patent Document 2) Korean Patent No. 10-1670092 (Oct. 21, 2016) disclose a fructooligosaccharide composition, a method for preparing the same and use thereof.

SUMMARY OF THE INVENTION

Therefore, the present invention has been made in view of the above problems, and it is an object of the present invention to develop and provide a novel fructooligosaccharide-based prebiotic composition.

In accordance with the present invention, the above and other objects can be accomplished by the provision of a prebiotic composition containing butyryl-fructooligosaccharides.

Preferably, the butyryl-fructooligosaccharides may have two to nine fructose linked to glucose and may have a butyryl functional group linked thereto.

Preferably, one to four butyryl functional groups including the butyryl functional group may be linked to the fructooligosaccharides.

Preferably, the composition may facilitate proliferation of intestinal beneficial bacteria and inhibit growth of harmful intestinal bacteria.

Preferably, the beneficial bacteria may include one or more selected from *Bifidobacterium, Lactobacillus, Lactococcus* and *Streptococcus*.

Preferably, the *Bifidobacterium* may include any one selected from *Bifidobacterium bifidum, Bifidobacterium longum, Bifidobacterium catenulatum* and *Bifidobacterium animalis*.

Preferably, the *Lactobacillus* may include any one selected from *Lactobacillus casei*, and *Lactococcus lactis*.

Preferably, the *Streptococcus* may be *Streptococcus* thermophiles.

Preferably, the harmful bacteria may include any one selected from *Staphylococcus aureus, Escherichia coli, Enterococcus faecalis, Clostridium butyricum, Prevotella intermedia* and *Clostridium ramosum*.

BRIEF DESCRIPTION OF THE DRAWINGS

The above and other objects, features and other advantages of the present invention will be more clearly understood from the following detailed description taken in conjunction with the accompanying drawings, in which.

Figure 8:
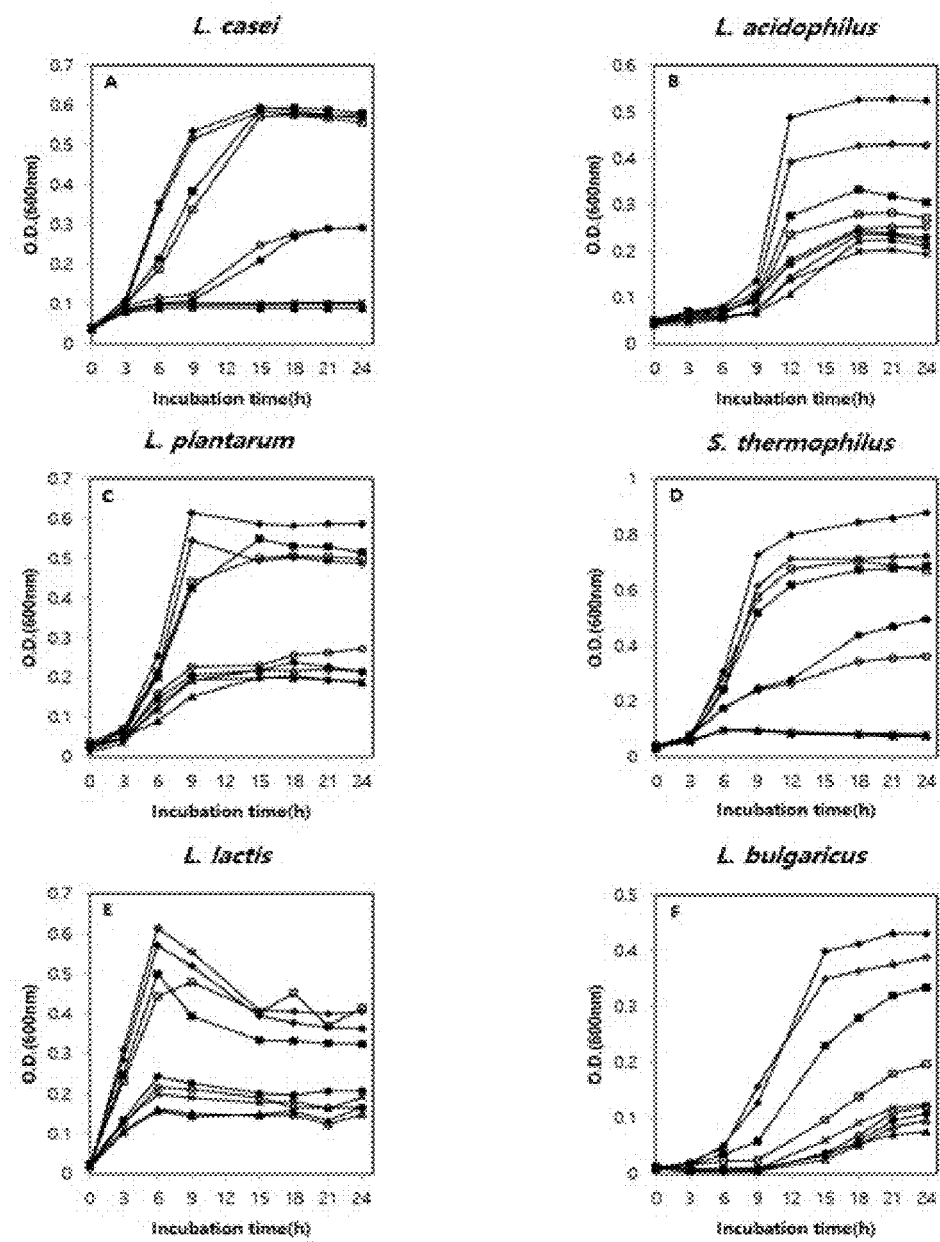
Figure 9:
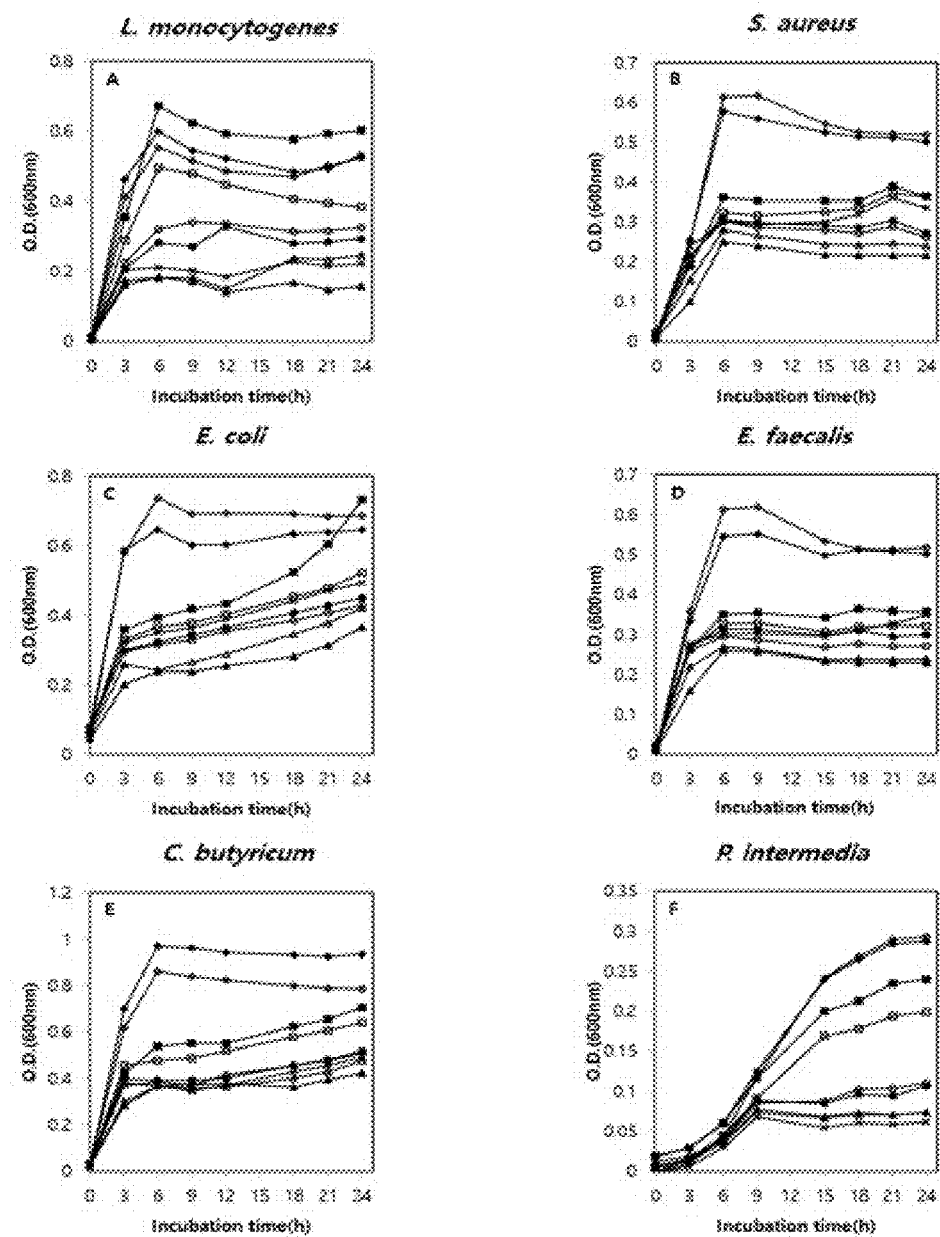
Figure 10:
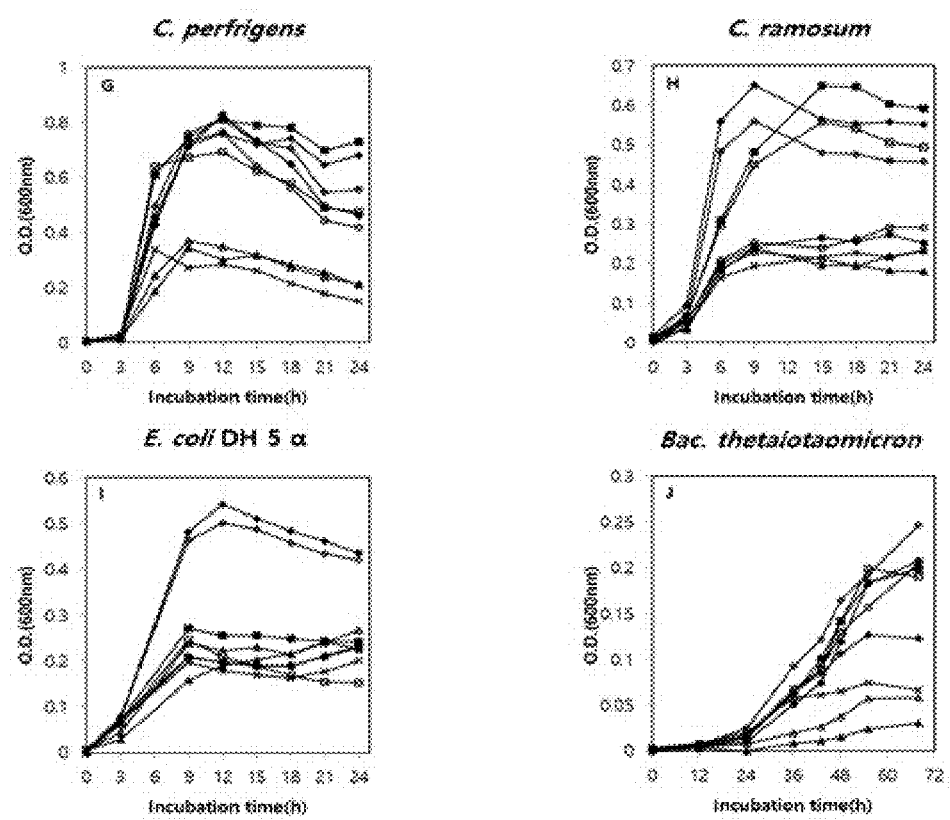
Figure 11:
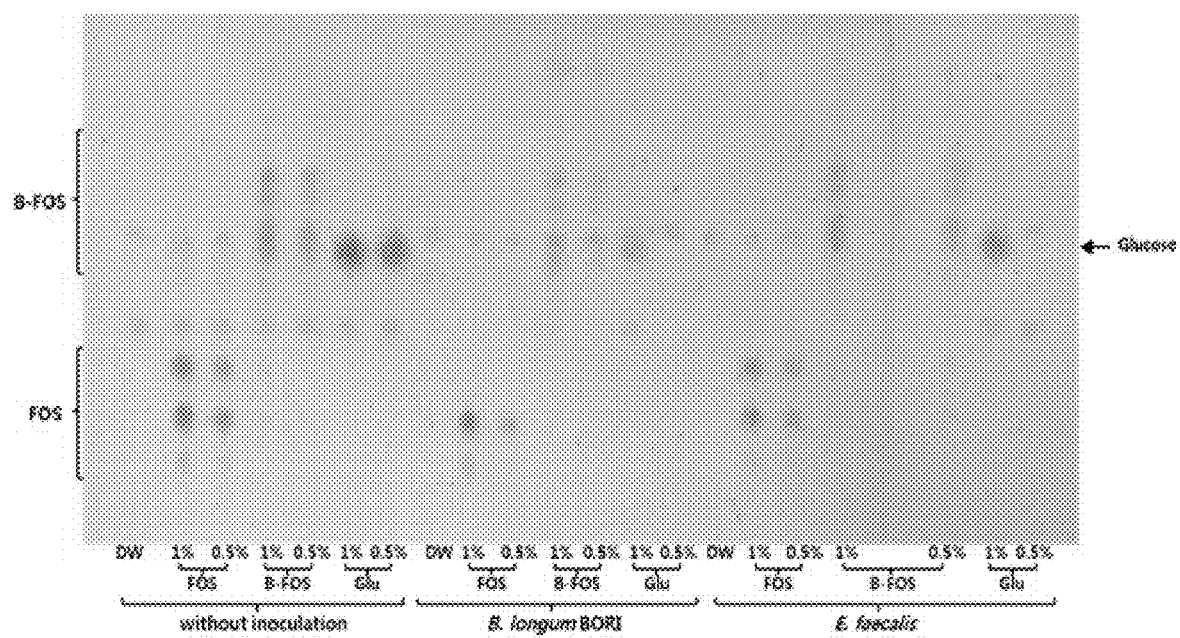
Figure 12:
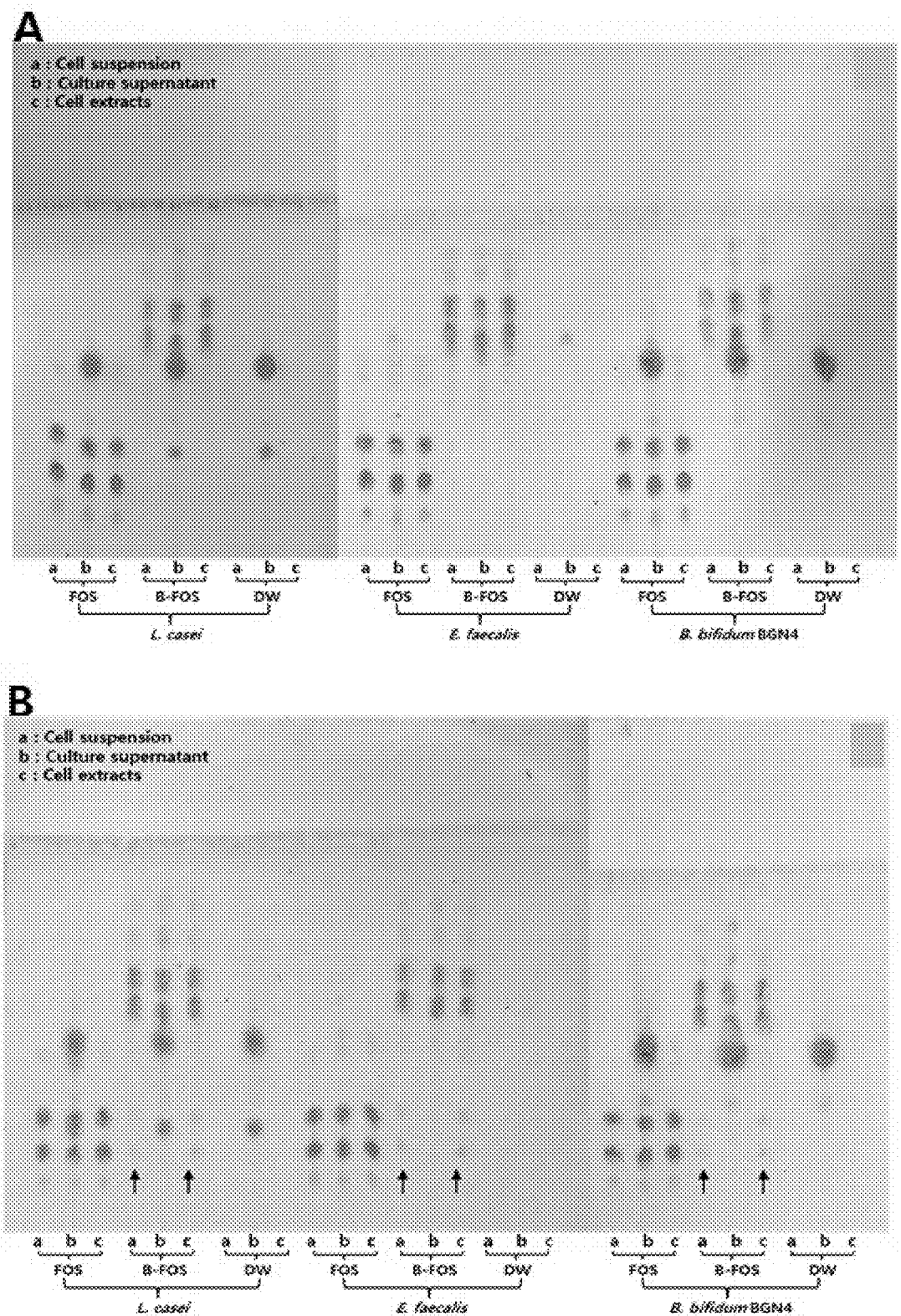
Figure 13:
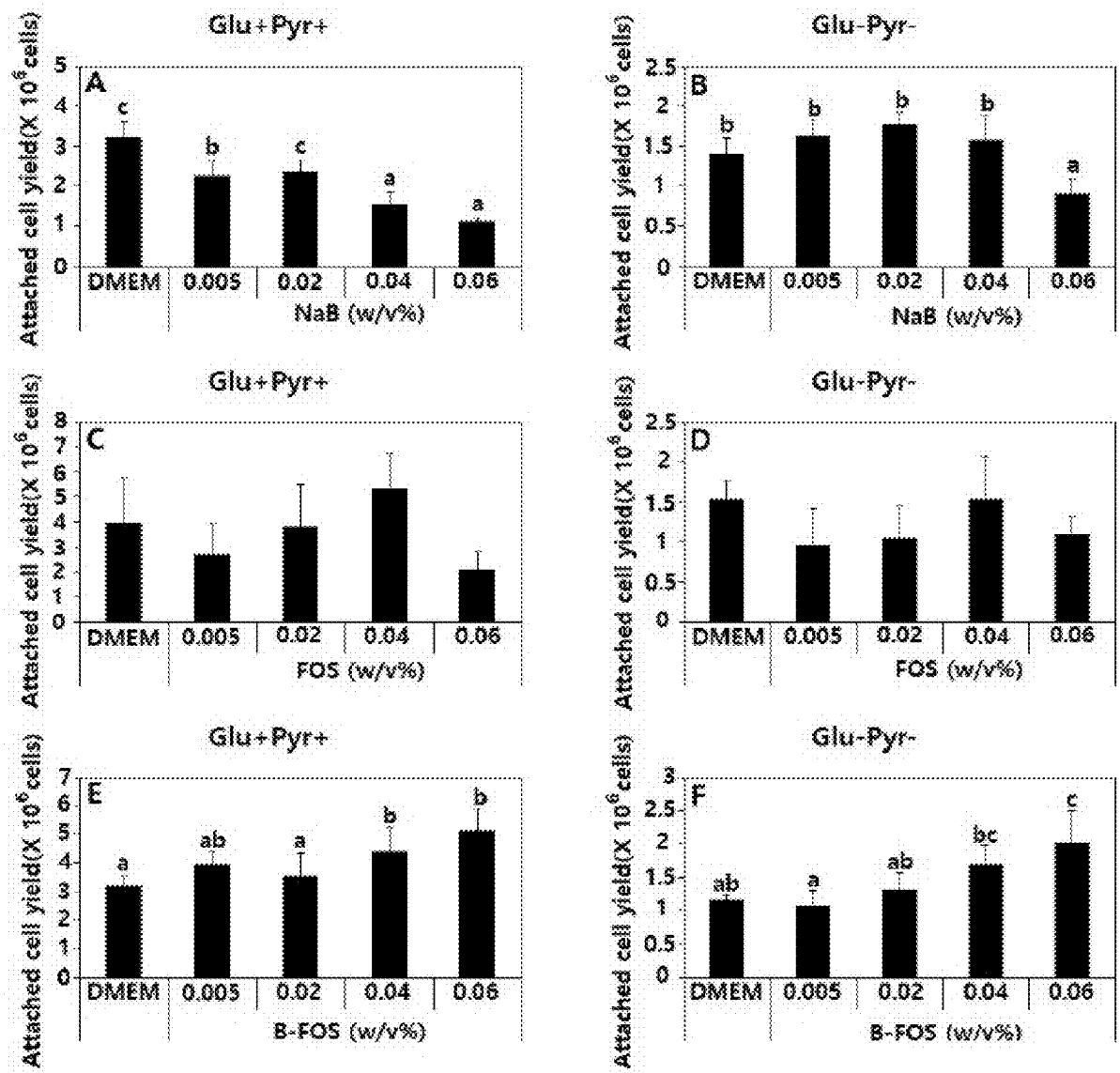
Figure 14:
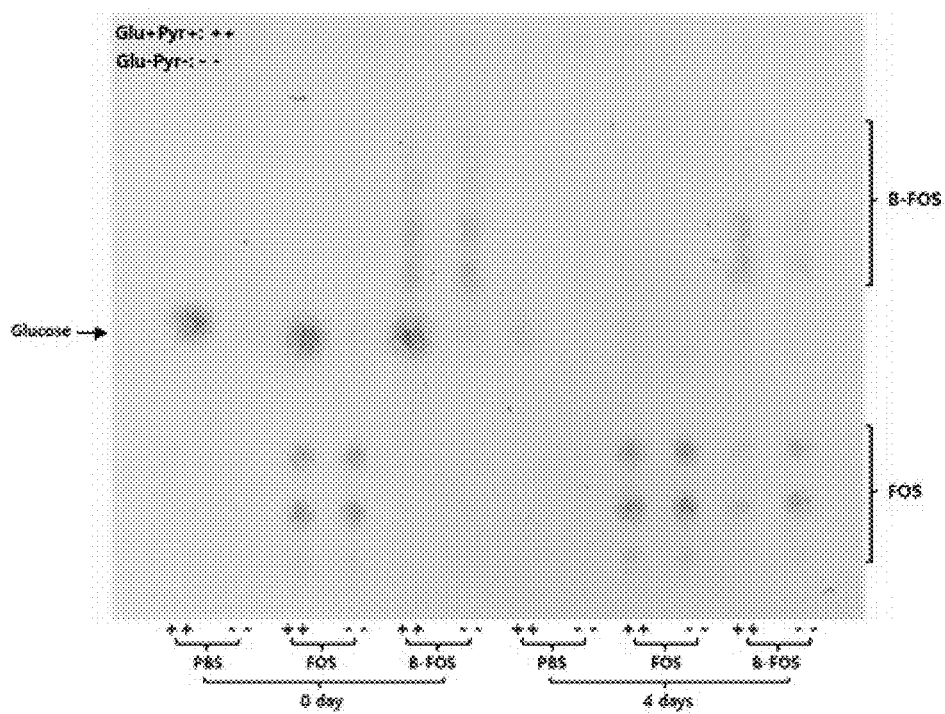
Figure 15:
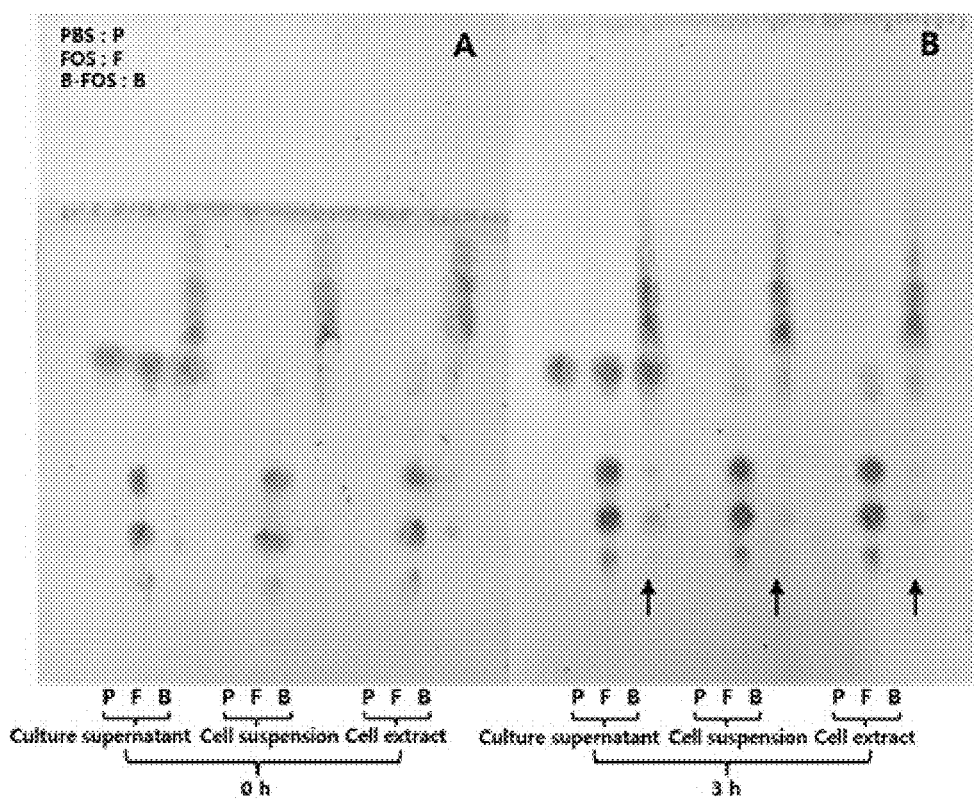
Figure 16:
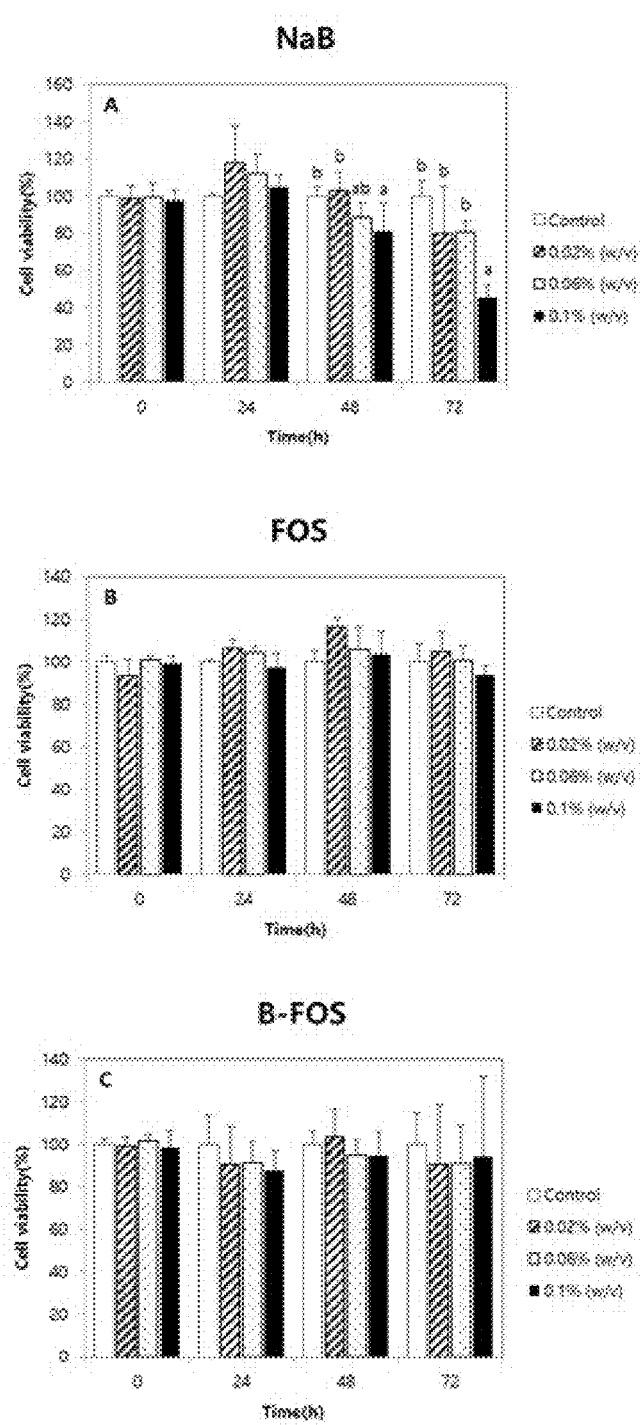
Figure 17:
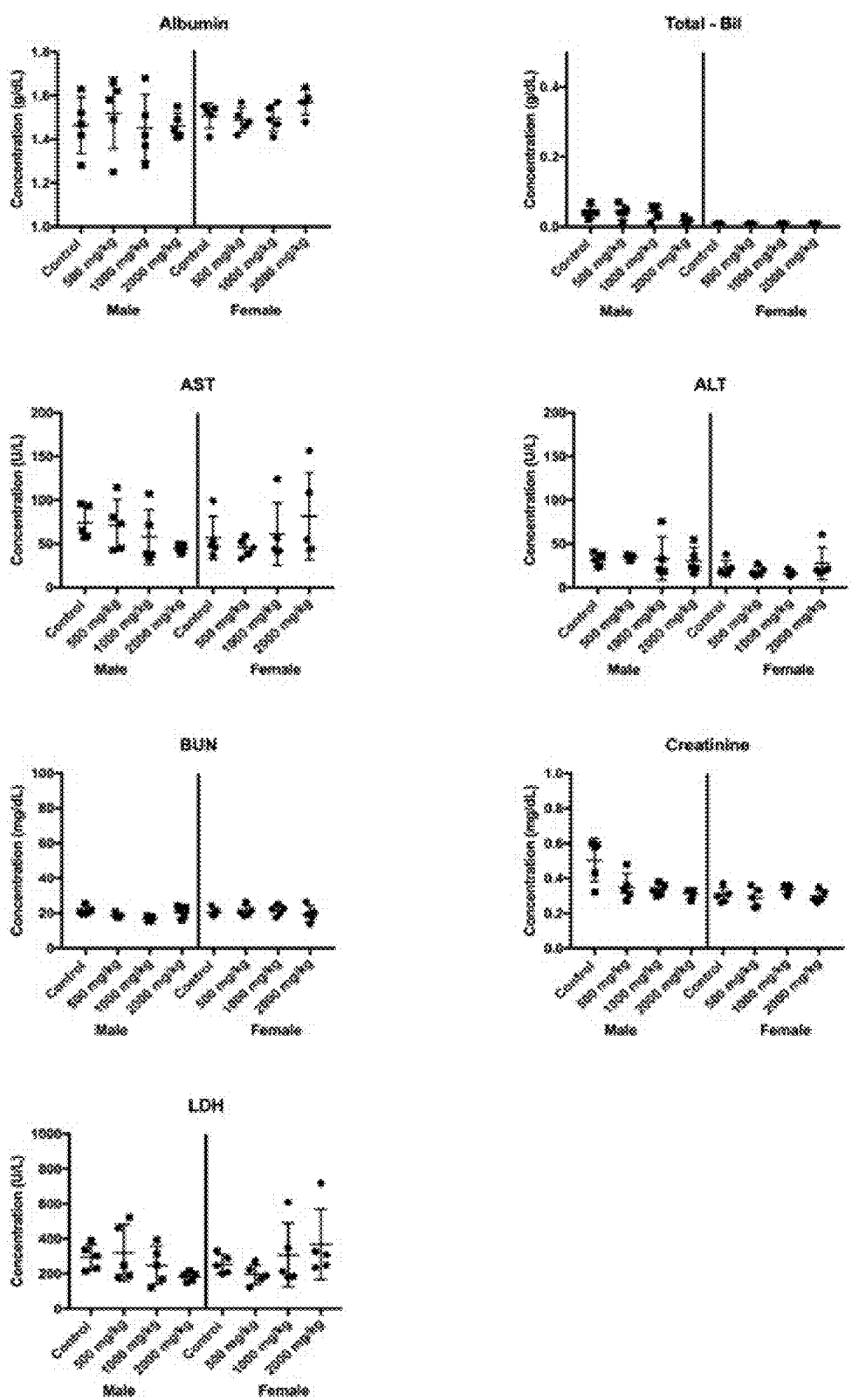
Figure 18:
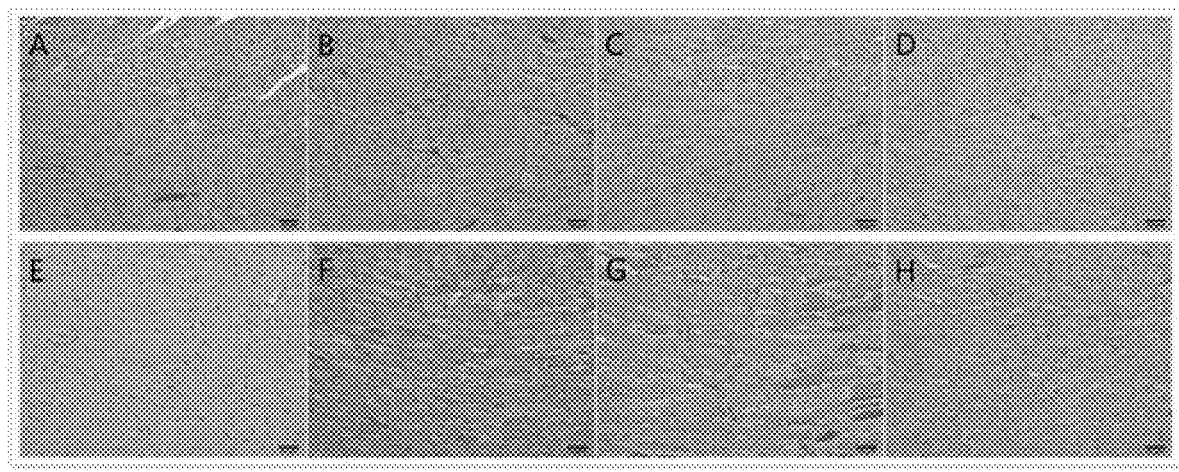
Figure 19:
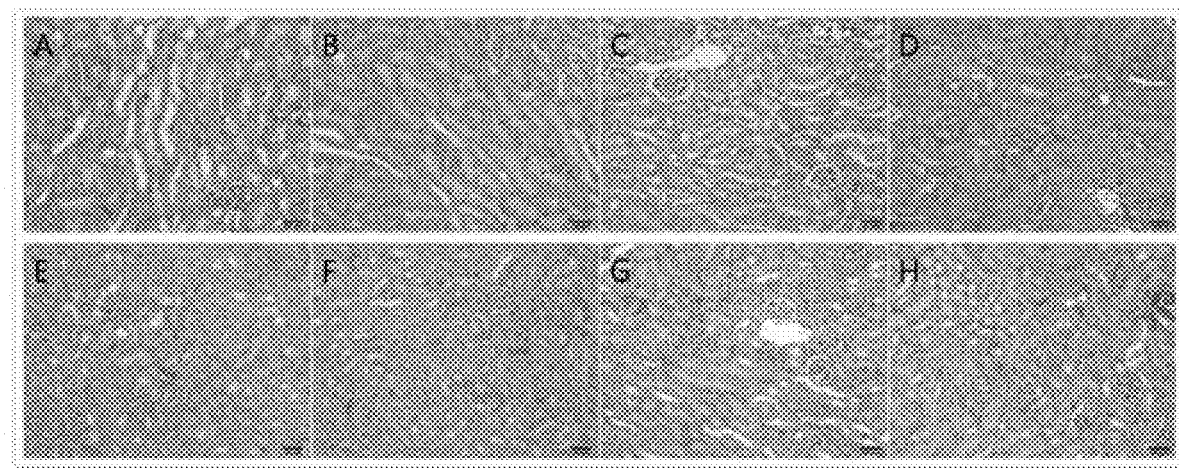
Figure 20:
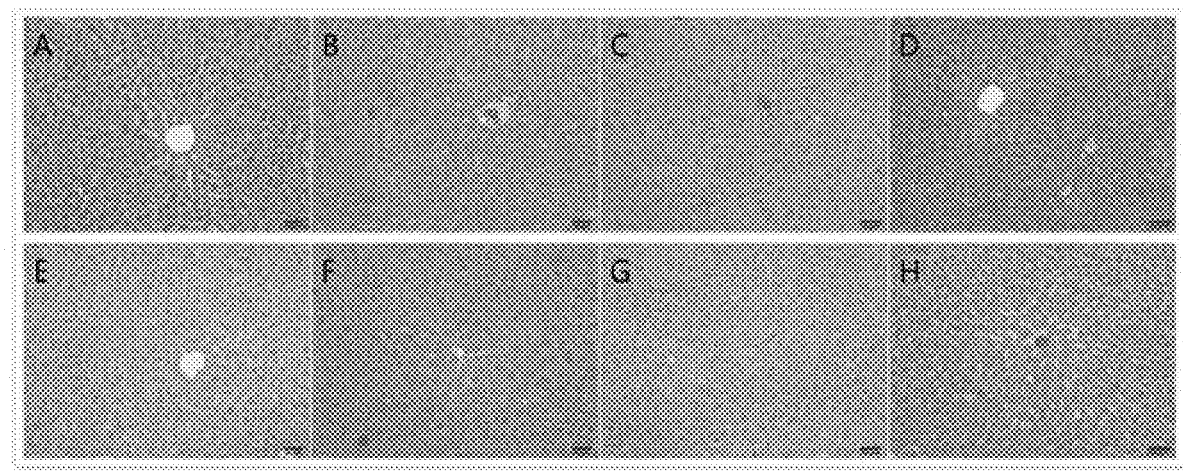
Figure 21:
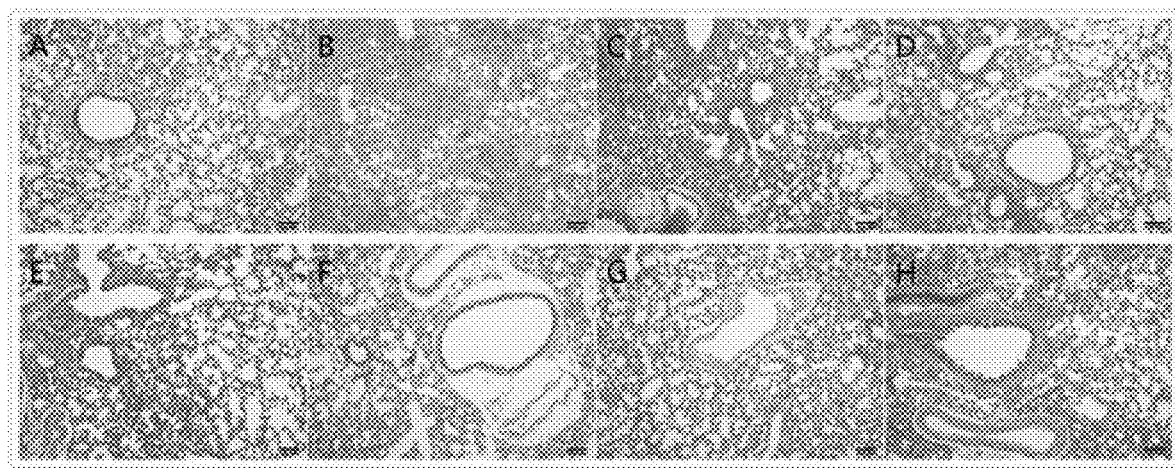
Figure 22:
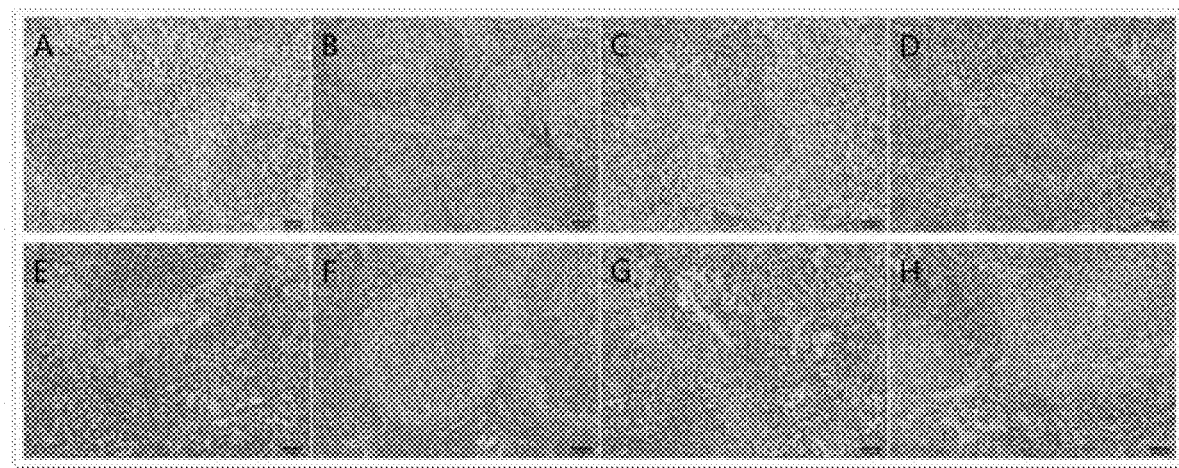
Figure 23:
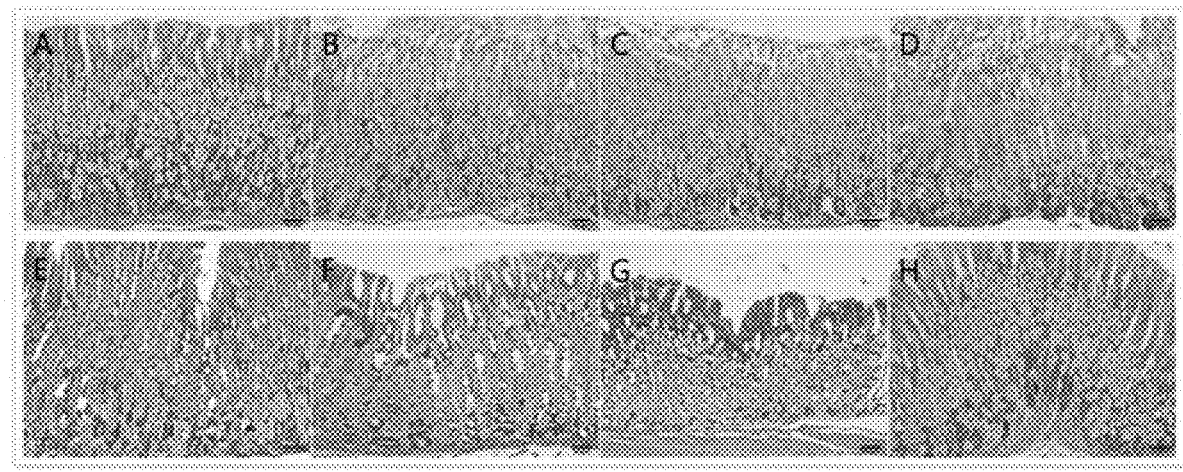
Figure 24:
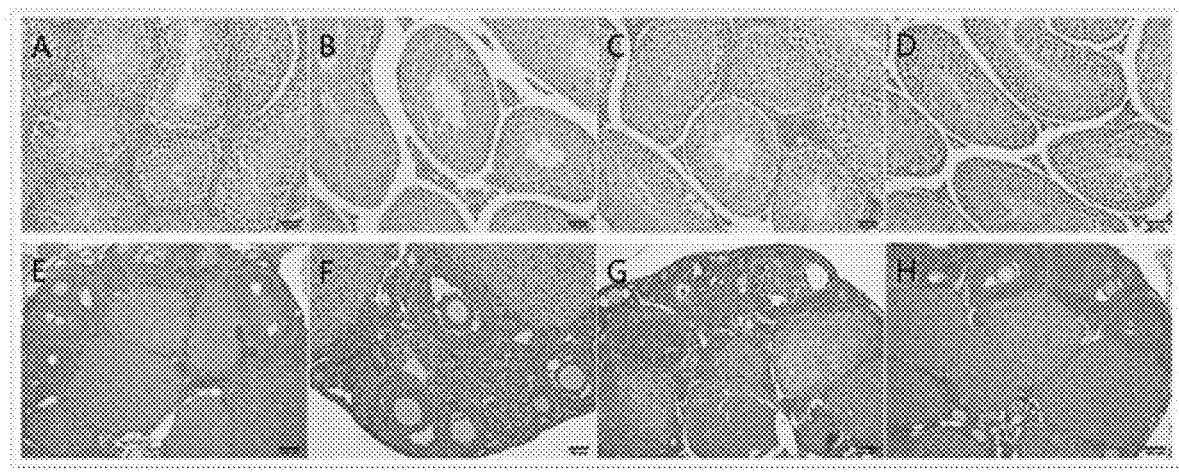

*thermophilum* (H) (△: 0.5% (w/v) NaB, □: 0.5% (w/v) FOS, ○: 0.5% (w/v) B-FOS, ◇: 0.5% (w/v) glucose, ▲: 1% (w/v) NaB, ■: 1% (w/v) FOS, ●: 1% (w/v) B-FOS, ▲: 1% (w/v) glucose, x: distilled water (sterile DI water));

FIG. 8 shows measurement results of growth curves of lactic acid bacteria of *L. casei* (A), *L. acidophilus* (B), *L. plantarum* (C), *S. thermophilus* (D), *L. lactis* (E), and *L. bulgaricus* (F) (△: 0.5% (w/v) NaB, □: 0.5% (w/v) FOS, ○: 0.5% (w/v) B-FOS, ◇: 0.5% (w/v) glucose, ▲: 1% (w/v) NaB, ■: 1% (w/v) FOS, ■: 1% (w/v) B-FOS, ♦: 1% (w/v) glucose, x: distilled water (sterile DI water));

FIG. 9 shows measurement results of growth curves of non-probiotic strains of *L. monocytogenes* (A), *S. aureus* (B), *E. coli* (C), *E. faecalis* (D), *C. butyricum* (E), and *P. intermedia* (F) (△: 0.5% (w/v) NaB, □: 0.5% (w/v) FOS, ○: 0.5% (w/v) B-FOS, ◇: 0.5% (w/v) glucose, ▲1% (w/v) NaB, ■: 1% (w/v) FOS, ●: 1% (w/v) B-FOS, ♦: 1% (w/v) glucose, x: distilled water (sterile DI water));

FIG. 10 shows measurement results of growth curves of non-probiotic strains of *C. perfringens* (G), *C. ramosum* (H), *E. coli* DH5α (I), and *Bac. thetaiotaomicron* (J) (◇: 0.5% (w/v) NaB, □: 0.5% (w/v) FOS, ○: 0.5% (w/v) B-FOS, ◇: 0.5% (w/v) glucose, ▲: 1% (w/v) NaB, ■: 1% (w/v) FOS, ●: 1% (w/v) B-FOS, ♦: 1% (w/v) glucose, x: distilled water (sterile DI water));

FIG. 11 shows TLC results of culture supernatants of *Bifidobacterium longum* BORI and *Enterococcus faecalis* (*E. faecalis*);

FIG. 12 shows results of TLC analysis of a cell suspension, a cell extract and a culture supernatant before (A) and after (B) reaction with FOS and B-FOS;

FIG. 13 shows the number of cells measured at different concentrations of the substance after adding NaB, FOS and B-FOS at a concentration of 0 to 0.06% (w/v) depending on presence of glucose and pyruvate, and culturing for 4 days (A: Glu+Pyr+NaB+, B: Glu–Pyr–NaB+, C: Glu+Pyr+FOS+, D: Glu–Pyr–FOS+, E: Glu+Pyr+B–FOS+, F: Glu–Pyr–B–FOS+);

FIG. 14 shows results of TLC analysis of the culture supernatant after culturing Caco-2 cells in a medium containing FOS and B-FOS;

FIG. 15 shows TLC analysis before (A) and after (B) reacting a culture supernatant, a cell suspension and a cell extract of Caco-2 cells with FOS and B-FOS;

FIG. 16 shows of cytotoxicity confirmed by MTT analysis to confirm the effects of NaB (A), FOS (B) and B-FOS (C) on cell viability of Caco-2 cells;

FIG. 17 shows biochemical indicators of blood serum of female and male mice after exposure to B-FOS;

FIG. 18 shows heart tissue dyeing results of ICR mice to which B-FOS is administered ((A) to (D): male mouse, (E) to (H): female mouse, and control group, 500 mg/kg, 1000 mg/kg and 2000 mg/kg in this order from the left);

FIG. 19 shows kidney tissue dyeing results of ICR mice to which B-FOS is administered ((A) to (D): male mouse, (E) to (H): female mouse, and control group, 500 mg/kg, 1000 mg/kg and 2000 mg/kg in this order from the left);

FIG. 20 shows liver tissue dyeing results of ICR mice to which B-FOS is administered ((A) to (D): male mouse, (E) to (H): female mouse, and control group, 500 mg/kg, 1000 mg/kg and 2000 mg/kg in this order from the left);

FIG. 21 shows lung tissue dyeing results of ICR mice to which B-FOS is administered ((A) to (D): male mouse, (E) to (H): female mouse, and control group, 500 mg/kg, 1000 mg/kg and 2000 mg/kg in this order from the left);

FIG. 22 shows spleen tissue dyeing results of ICR mice to which B-FOS is administered ((A) to (D): male mouse, (E) to (H): female mouse, and control group, 500 mg/kg, 1000 mg/kg and 2000 mg/kg in this order from the left);

FIG. 23 shows stomach tissue dyeing results of ICR mice to which B-FOS is administered ((A) to (D): male mouse, (E) to (H): female mouse, and control group, 500 mg/kg, 1000 mg/kg and 2000 mg/kg in this order from the left); and FIG. 24 shows testicle and ovary tissue dyeing results of ICR mice to which B-FOS is administered ((A) to (D): male mouse, (E) to (H): female mouse, and control group, 500 mg/kg, 1000 mg/kg and 2000 mg/kg in this order from the left).

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

The present invention provides a prebiotic composition containing butyryl-fructooligosaccharides (B-FOS).

Fructooligosaccharide (FOS) refers to a polymer of one glucose molecule and fructose, commonly, 2 to 9 fructose molecules.

The term "butyryl-fructooligosaccharide" used herein refers to fructooligosaccharide as described above that has a butyryl group linked, via an ester bond, to OH of glucose or fructose in the fructooligosaccharide, preferably a fructooligosaccharide that has one or four butyryl groups linked thereto.

Most intestinal microbes are anaerobic bacteria that obtain energy by fermenting carbohydrates and produce organic acid as a fermentation product. Fructooligosaccharides (FOSs) are oligosaccharides which can be used by intestinal microbes upon reaching the large intestine because they are not digested in the stomach and small intestines, which are known to be used as specific substrates of Bifidobacteria and *Lactobacillus* in large intestines. FOS may be beneficial to humans by increasing the number of intestinal probiotic strains, but harmful bacteria and non-probiotic strains each capable of metabolizing FOS in the intestines may cause adverse effects. Accordingly, as a solution to this, according to the present invention, butyryl-fructooligosaccharides (B-FOSs) including butyrate and FOS (fructooligosaccharides) linked to each other via an ester bond are newly synthesized and provided as a prebiotics.

The B-FOS is synthesized by adding butyric acid to an aqueous fructooligosaccharide (FOS) solution, followed by mixing. A concentration of fructooligosaccharide is from 10% to 70% (w/v), the fructooligosaccharide and butyric acid are mixed in a ratio of 10:1 to 1:1 at a temperature of 100° C. or less, and the mixture is reacted for 30 minutes to 3 hours and then neutralized with a NaOH solution to complete the reaction.

Meanwhile, the prebiotic composition of the present invention preferably facilitates the proliferation of intestinal beneficial bacteria and inhibits the growth of harmful intestinal bacteria, and the beneficial bacteria preferably include one or more selected from *Bifidobacterium, Lactobacillus, Lactococcus* and *Streptococcus*, more preferably, includes one or more selected from *Bifidobacterium bifidum, Bifidobacterium longum, Bifidobacterium catenulatum, Bifidobacterium animalis, Lactobacillus casei, Lactococcus lactis* and *Streptococcus thermophilus*.

In addition, the harmful bacteria preferably include any one selected from *Staphylococcus aureus, Escherichia coli,*

*Enterococcus faecalis, Clostridium butyricum, Prevotella intermedia* and *Clostridium ramosum*.

The present invention demonstrated that B-FOS, which is a novel synthetic substance developed by the present inventors, facilitates the growth of beneficial bacteria and is consumed by beneficial bacteria to produce lactic acid, acetic acid and butyric acid as metabolites, but does not affect the growth of non-probiotic strains including harmful bacteria. In addition, B-FOS is degraded on the wall of cells or in cells to produce FOS and butyrate. The produced FOS and butyrate are considered to have an influence on inhibiting or facilitating the growth of cells. In addition, B-FOS facilitates the proliferation of Caco-2 cells, which indicates that B-FOS is degraded on the wall of Caco-2 cells or inside or outside cells to produce FOS and butyrate, and the produced butyrate is used as an energy source of Caco-2 cells. Hereinafter, the present invention will be described in more detail with reference to the following Example and Test example, and the scope of the present invention is not limited to the Example and Test example, and also includes modifications of technical concepts equivalent thereto.

All results of the following tests are indicated as mean±standard deviation. Statistical analysis was conducted using Statistical Package for the Social Sciences (SPSS, Ver. 22.0, SPSS Inc., Chicago, Ill., USA). One-way analysis of variance was conducted as statistical processing. If there was a significant difference, post-hoc testing was conducted by Duncan's multiple range test, and regarding transepithelial electrical resistance (TEER) of Caco-2 cells, the significant difference between means was tested by least significant difference test (LSD). Unless equal variance assumption was satisfied, analysis was conducted by Welch's test, and if there was a significant difference, post-hoc testing was conducted by Games-Howell test. $P<0.05$ was determined to be statistically significant.

Example 1: Purification and Structure of Butyryl-Fructooligosaccharides (B-FOS)

(1) B-FOS Synthesis

B-FOS was synthesized by adding butyric acid to an aqueous fructooligosaccharide (FOS) solution, followed by mixing. A concentration of fructooligosaccharides was 50% (w/v), the fructooligosaccharides and butyric acid were mixed in a ratio of 10:1, and the mixture was reacted at a temperature of 50° C. for 3 hours and was then neutralized with a NaOH solution to complete the reaction.

(2) B-FOS Purification

Figure 1:
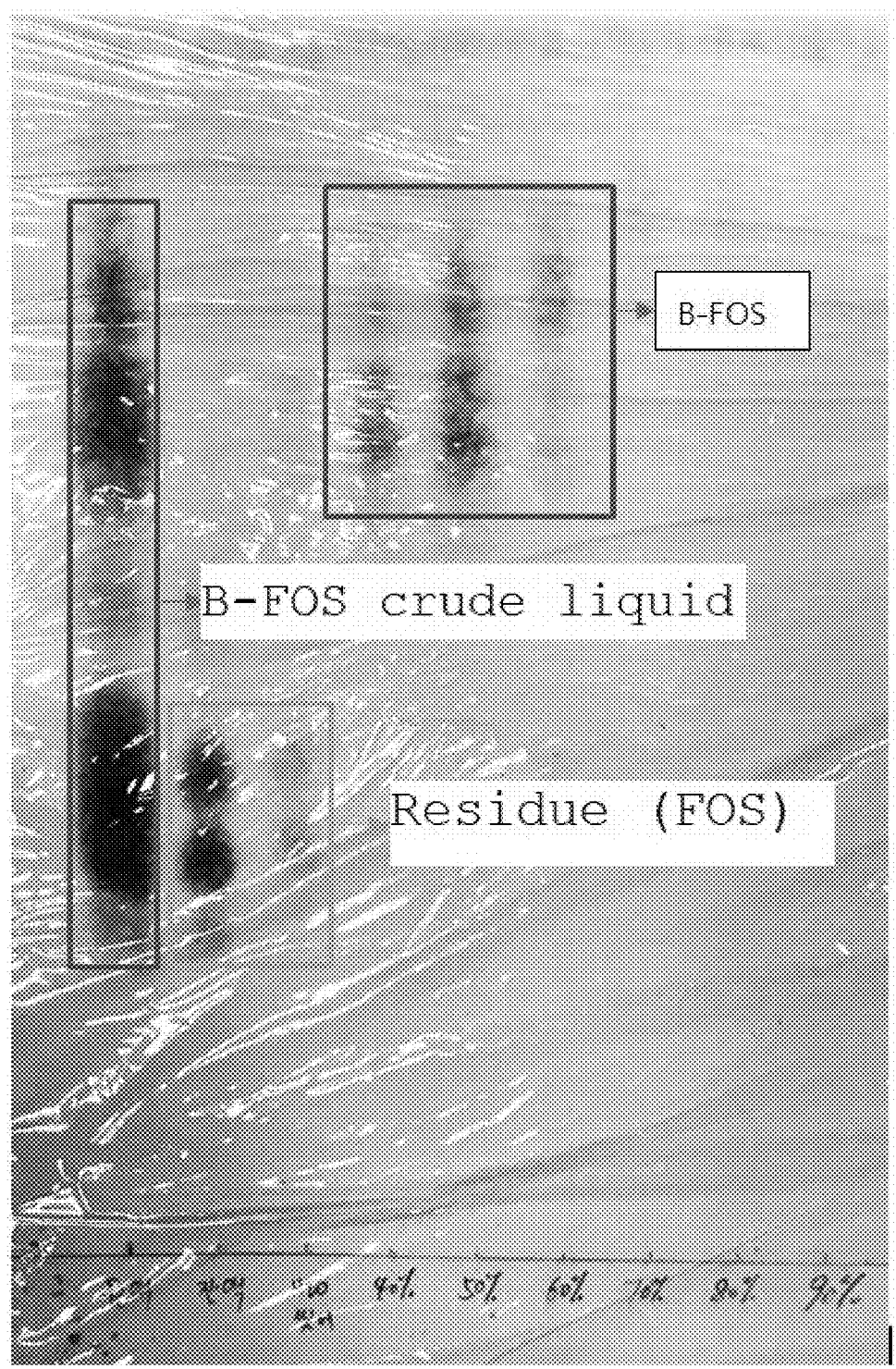
FIG. 1 shows results of thin layer chromatography of B-FOS.

The synthesized B-FOS was purified by column chromatography using Diaion HP20 (Mitsubishi, Tokyo, Japan) as a synthetic adsorber. A 50×5 cm glass Econo-Column (Bio-Rad, Hercules, Calif., USA) was filled with a predetermined amount of Diaion HP20 and washed with an ethanol solution and triple distilled water. B-FOS purified, as a developing solvent, using 1-propanol/tertiary distilled water/ethyl acetate (7:2:1, v/v) was added dropwise to a silica gel plate 60F254 (Merck, Darmstadt, Germany). After spraying a sulfuric acid/ethanol (1:9, v/v) solution as a color developing reagent onto the plate, the plate was heated in a dried oven at 110° C. for 10 minutes (FIG. 1). FIG. 1 shows results of thin layer chromatography of B-FOS.

Figure 2:
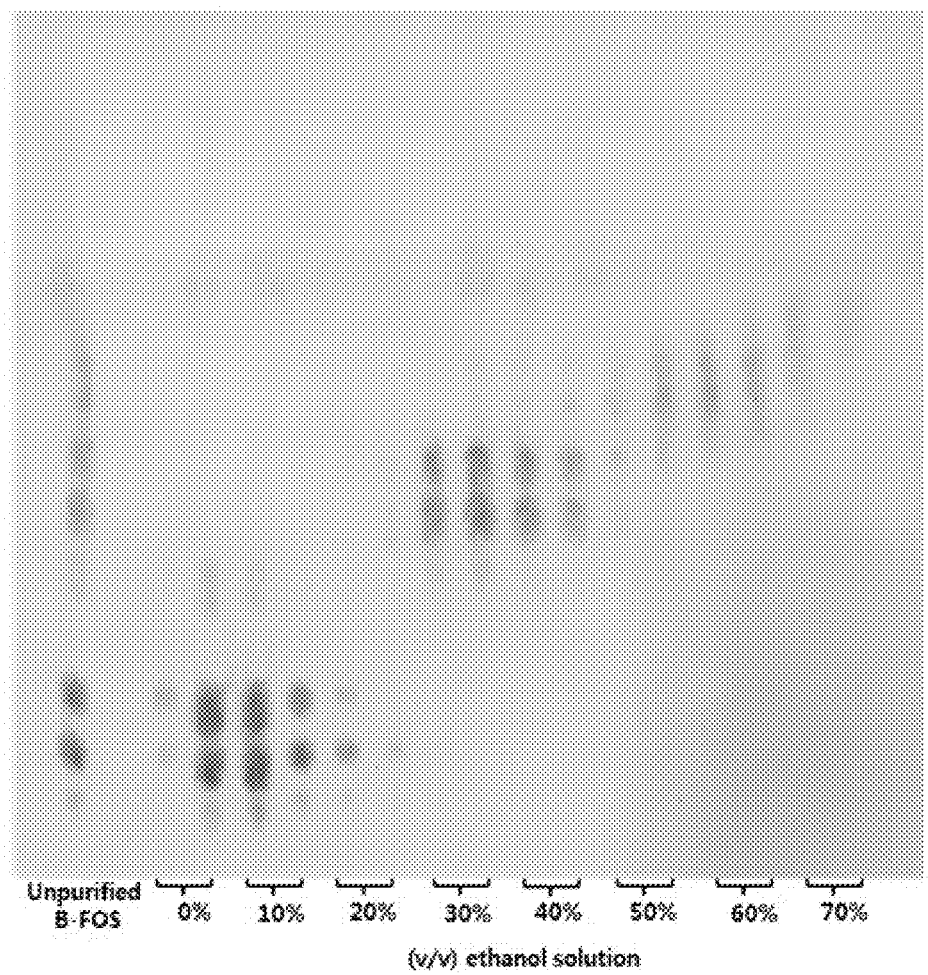
FIG. 2 shows results of thin layer chromatography of B-FOS in a 0-70% (v/v) aqueous ethanol solution.

A non-purified B-FOS solution was diluted (×4) with tertiary distilled water, loaded and then eluted with a 0-70% (v/v) aqueous ethanol solution. In the process of purification using column chromatography, as a result of thin layer chromatography (TLC) of the substance eluted with the 0-70% (v/v) aqueous ethanol solution, B-FOS purified in a 30-70% (v/v) aqueous ethanol solution was identified (FIG. 2). FIG. 2 shows results of thin layer chromatography of B-FOS in a 0-70% (v/v) aqueous ethanol solution. Excluding the solution eluted with the 0-20% (v/v) aqueous ethanol solution, the portion eluted with the 30-70% (v/v) aqueous ethanol solution was harvested. The purified B-FOS was concentrated using a speed vacuum concentrator ScanSpeed40 (Labogene, Lynge, Denmark) and lyophilized in a lyophilizer (Ilshin biobase, Yangju, Korea).

(3) Structural Analysis of B-FOS

Figure 3:
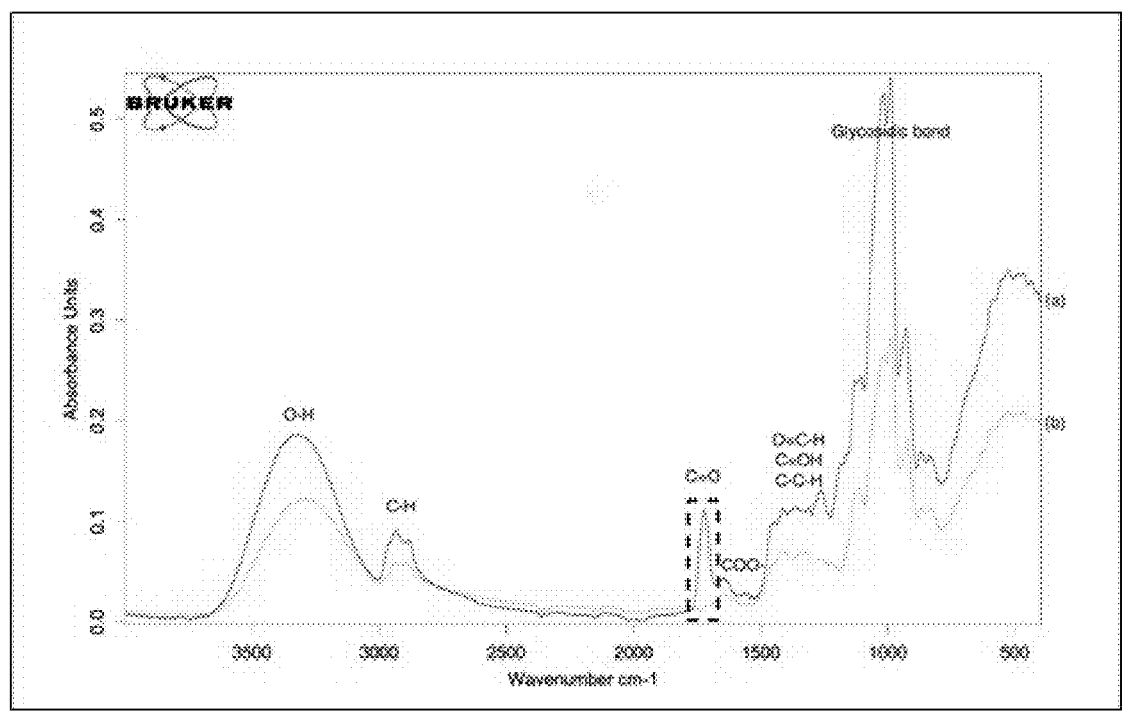
FIG. 3 shows results of FT-IR spectrum of B-FOS.

In order to analyze the structure of B-FOS, active group linkage analysis by FT-IR and mass analysis by MALDITOF were conducted. From the FT-IR spectrum, excluding the peak plotted at 1720.45 $cm^{-1}$, B-FOS and FOS had considerably similar chemical bonds. The peak was present only in B-FOS and formed an ester bond (FIG. 3). FIG. 3 shows FT-IR spectrum results of B-FOS. That is, B-FOS is a substance including butyrate and fructooligosaccharides (FOS) linked to each other via an ester bond.

Figure 4:
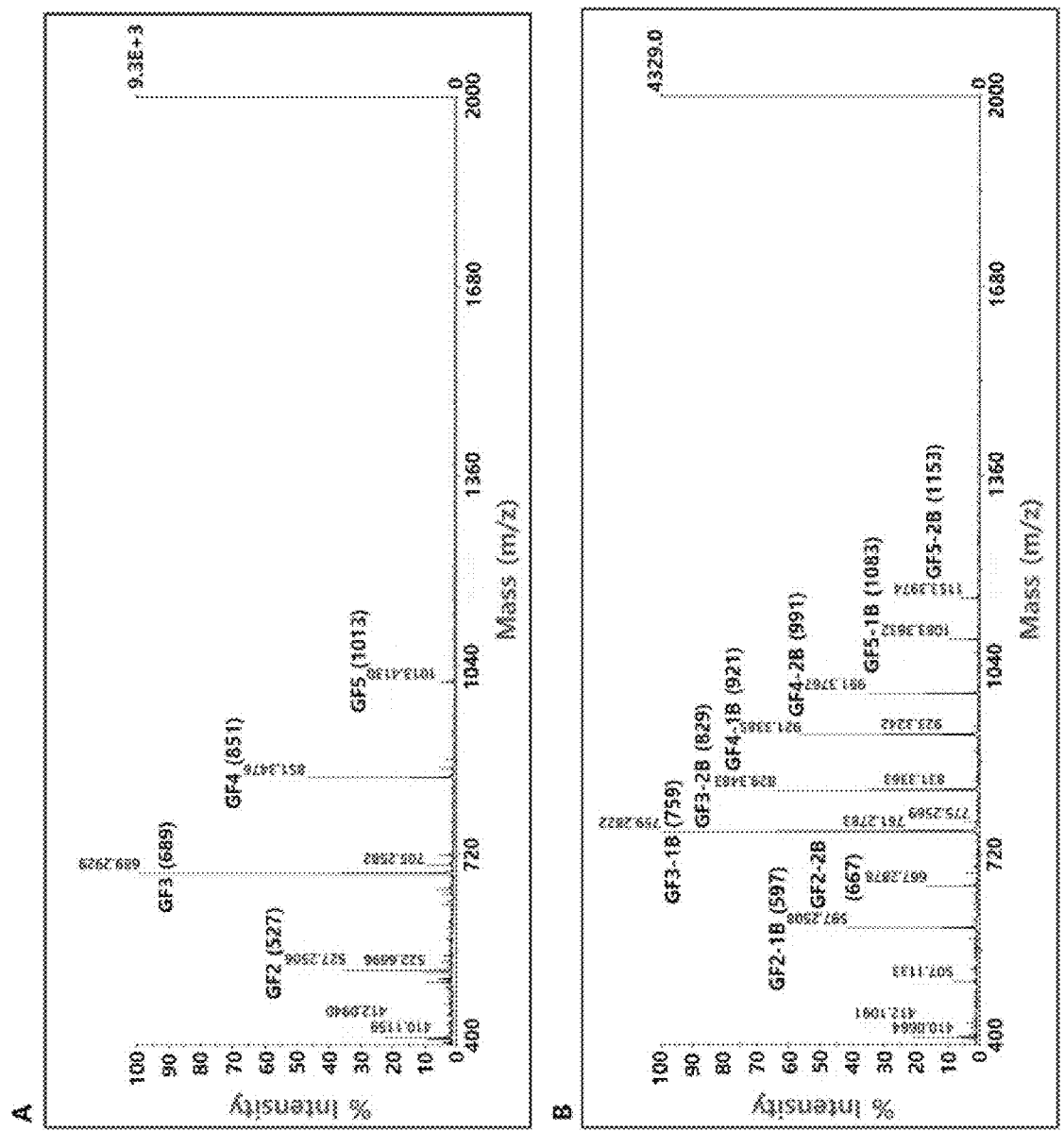
FIG. 4 shows results of MALDI-TOF analysis on FOS and B-FOS (A: FOS, B: B-FOS)

MALDI-TOF analysis showed that FOS, as a control substance, consists of GF2, GF3, GF4 and GF5, each including fructose bound to glucose (FIG. 4A). B-FOS consists of GF2-1B, GF2-2B, GF3-1B, GF3-2B, GF4-1B, GF4-2B, GF5-1B and GF5-2B, each including a butyryl group bound to the structure of FOS (FIG. 4B). FIG. 4 shows MALDI-TOF analysis results of FOS and B-FOS (A: FOS, B: B-FOS). Accordingly, B-FOS is found to be a substance having one or two butyrate molecules linked to FOS via an ester bond.

Meanwhile, hereinafter, a mixture including GF2-1B, GF2-2B, GF3-1B, GF3-2B, GF4-1B, GF4-2B, GF5-1B and GF5-2B was purified and separated, and was then used as B-FOS, and the prebiotic effects of B-FOS were tested.

(4) Changes of B-FOS Under Acidic and Heat Treatment Conditions

To check whether or not B-FOS was degraded under acidic conditions, 900 μl of phosphate buffer saline (PBS) having a pH of 2, 3 or 4 adjusted with a 1N hydrochloric acid solution was reacted with 100 μl of a 10% (w/v) B-FOS solution at room temperature for 30 minutes, 1 hour and 3 hours. Whether or not degradation by heat occurred was checked by heat-treating 1 mL of a 1% (w/v) B-FOS solution with boiling water for 15 minutes. Whether or not B-FOS was degraded was checked by TLC. TLC conditions were the same as those used for B-FOS purification.

Figure 5:
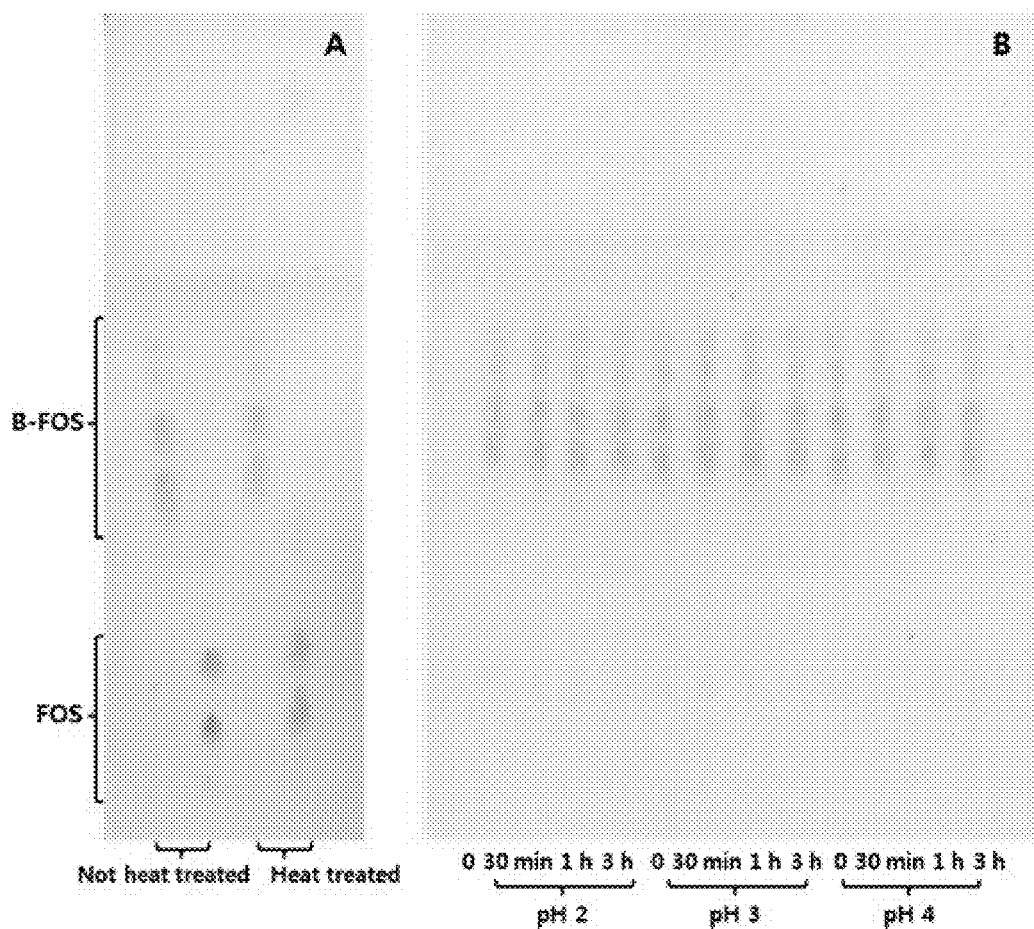
FIG. 5 shows results of safety analysis upon acid and heat treatment (A: fructooligosaccharides (FOS) and B-FOS heat-treated with boiling water for 15 minutes, B: B-FOS exposed to PBS having a pH adjusted to 2-4 for 30 minutes, 1 hour and 3 hours)

TLC analysis results of the fructooligosaccharides (FOS) and B-FOS, which underwent heat-treatment with boiling water for 15 minutes, and B-FOS exposed to PBS having a pH adjusted to 2-4 for 30 minutes, 1 hour and 3 hours showed that the heat-treated FOS and B-FOS had no change in TLC and were stable under these conditions. In addition, B-FOS had no change in TLC for 3 hours under acidic conditions (pH 2-4) and was stable under these conditions (FIG. 5). FIG. 5 shows results of safety analysis upon acid and heat treatment (A: fructooligosaccharides (FOS) and B-FOS heat-treated with boiling water for 15 minutes, B: B-FOS exposed to PBS having a pH adjusted to 2-4 for 30 minutes, 1 hour and 3 hours).

Test Example 1: Effects of Sodium Butyrate (NaB), FOS, B-FOS and Glucose on Growth of Intestinal Bacteria (1) Production of Test Medium Bacteria strains used for the present test are shown in the following Table 1. All strains were obtained from the official institute of strain distribution or by the food microbiology laboratory of Seoul National University. Eight bifidobacteria strains, four *Lactobacillus* (lactic acid bacteria) strains, *lactis* KCTC 2013 (*Lactococcus lactis* subsp. *lactis* KCTC 2013), and *Streptococcus thermophilus* KCTC 3779 were sub-cultured in MRS supplemented with 0.05% (w/v) L-cysteine.HCl (de-Mann-Rogosa-Sharpe broth; Difco, Detroit, USA) at 37° C., twice every 18 hours prior to use. Other strains were sub-cultured in BHIB (brain-heart infusion broth; Difco) under the same culture conditions as above prior to use.

TABLE 1

| Test strains | Abbreviation |
|---|---|
| Bifidobacteria | |
| *Bifidobacterium bifidum* BGN4 | *B. bifidum* BGN4 |
| *B. longum* BORI | *B. longum* BORI |
| *B. catenulatum* KCTC 3221 | *B. catenulatum* |
| *B. animalis* KCTC 3219 | *B. animalis* |
| *B. adolescentis* KCTC 3216 | *B. adolescentis* |
| *B. longum* subsp. *longum* RD47 | *B. longum* RD47 |
| *B. longum* RD72 | *B. longum* RD72 |
| *B. thermophilum* KCCM 12097 | *B. thermophilum* |
| Lactic acid bacteria | |
| *Lactobacillus casei* KFRI 699 | *L. casei* |
| *L. acidophilus* KCTC 3168 | *L. acidophilus* |
| *L. plantarum* KFRI 708 | *L. plantarum* |
| *L. delbruekii* subsp. *bulgaricus* KCTC 3635 | *L. bulgaricus* |
| *Lactococcus lactis* subsp. *lactis* KCTC 2013 | *L. lactis* |
| *Streptococcus thermophilus* KCTC 3779 | *S. thermophilus* |
| Non-probiotic bacteria | |
| *Listeria monocytogenes* ATCC 10115 | *L. monocytogenes* |
| *Staphylococcus aureus* ACTC 6358 | *S. aureus* |
| *Escherichia coli* KCTC 1039 | *E. coli* |
| *Clostridium butyricum* KCTC 1871 | *C. butyricum* |
| *Enterococcus faecalis* KCTC 3511 | *E. faecalis* |
| *Prevotella intermedia* KCTC 5694 | *P. intermedia* |
| *Clostridium ramosum* KCTC 3323 | *C. ramosum* |
| *Escherichia coli* DH 5α | *E. coli* DH 5α |
| *Clostridium perfringens* KCTC 3269 | *C. perfringens* |
| *Bacteroides thetaiotaomicron* KCTC 5015 | *Bac. Thetaiotaomicron* |

A basal medium used for the bacterial growth test was sugar-free BHIB (MB Cell, Los Angeles, Calif., USA). The basal medium, to which PBS, NaB, FOS (BIFIDO) and glucose were each added, was compared with a medium supplemented with B-FOS. A 10% (w/v) solution of NaB, FOS, B-FOS and glucose in sterilized triple distilled water was prepared and filtered through a 0.2 μm membrane filter (Pall Corporation, Michigan, USA), which was then used. A 1% or 0.5% (w/v) solution of each substance in sterilized sugar-free BHIB was prepared and 198 μl of the solution was then seeded onto a 96-well plate.

(2) Measurement of Microbial Growth Curve

In order to remove glucose or other carbon source present in a culture medium of activated bacteria, cultured bacteria were centrifuged (15,000×g, 5 min), the supernatant was discarded and the precipitated bacteria were washed with PBS (pH 7.4) twice. The bacterial suspension released in PBS was seeded in a dose of 2 μl to a 96-well plate in each medium and cultured using a Whitley jar gassing system (Don Whitley Scientific, Shipley, UK) under anaerobic conditions at 37° C. for 24 hours. Bacterial proliferation was checked by measuring optical density (OD) of the culture solution, absorbance at 600 nm was measured with a microplate reader (BioRad, Hercules, Calif., USA) and a growth curve was made. Bacterial growth was analyzed by comparing maximum $OD_{600}$ values at a substance concentration of 1% (w/v). A medium in which bacteria were not cultured was set as a blank and a mean of values obtained by repeating the test three times was shown. The culture supernatant of the cultured bacteria was harvested for the following test.

Figure 6:
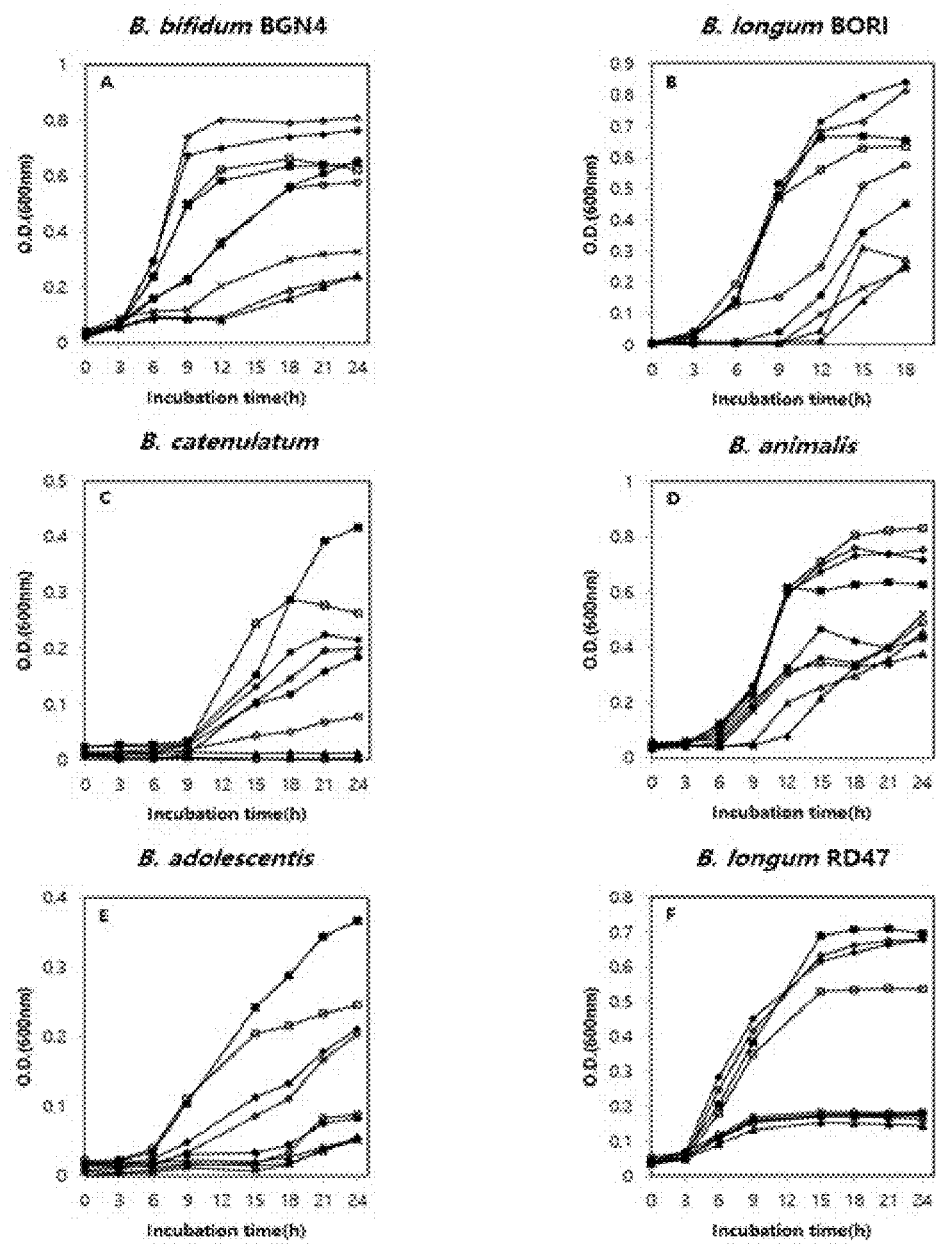
FIG. 6 shows measurement results of growth curves of Bifidobacteria strains of *B. bifidum* BGN4 (A), *B. longum* BORI (B), *B. catenulatum* (C), *B. animalis* (D), *B. adolescentis* (E), and *B. longum* RD47 (F) (△: 0.5% (w/v) NaB, □: 0.5% (w/v) FOS, ○: 0.5% (w/v) B-FOS, ◇: 0.5% (w/v) glucose, ▲: 1% (w/v) NaB, ■: 1% (w/v) FOS, ●: 1% (w/v) B-FOS, ◆: 1% (w/v) glucose, x: distilled water (sterile DI water))
Figure 7:
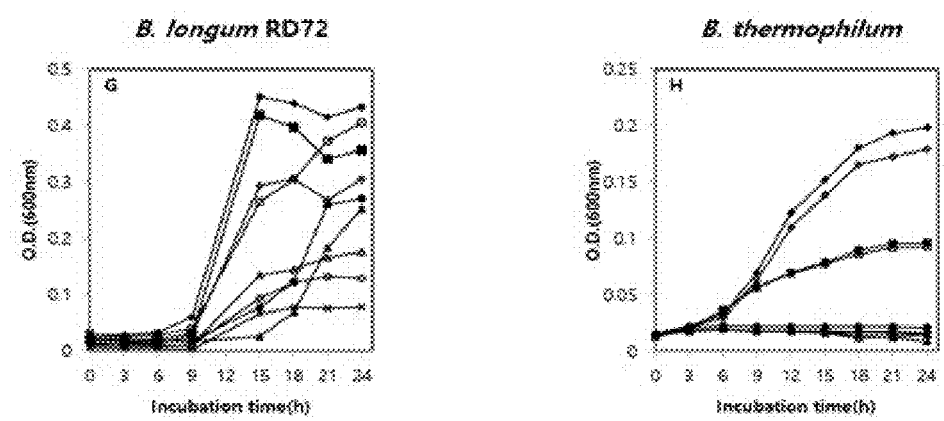
FIG. 7 shows measurement results of growth curves of Bifidobacteria strains of *B. longum* RD72 (G), and *B.*

When the concentration of the substance was 1% (w/v), maximum $OD_{600}$ of 14 strains were compared (FIGS. 6 to 10). FIG. 6 shows measurement results of growth curves of Bifidobacteria strains of *B. bifidum* BGN4, *B. longum* BORI, *B. catenulatum*, *B. animalis*, *B. adolescentis*, and *B. longum* RD47, FIG. 7 shows measurement results of growth curves of Bifidobacteria strains of *B. longum* RD72, and *B. thermophilum*, FIG. 8 shows measurement results of growth curves of lactic acid bacteria of *L. casei*, *L. acidophilus*, *L. plantarum*, *S. thermophilus*, *L. lactis*, and *L. bulgaricus*, FIG. 9 shows measurement results of growth curves of non-probiotic strains of *L. monocytogenes*, *S. aureus*, *E. coli*, *E. faecalis*, *C. butyricum*, and *P. intermedia*, and FIG. 10 shows measurement results of growth curves of non-probiotic strains of *C. perfringens*, *C. ramosum*, *E. coli* DH5α, and Bac. thetaiotaomicron (each medium; Δ: 0.5% (w/v) NaB, □: 0.5% (w/v) FOS, ○: 0.5% (w/v) B-FOS, ◇: 0.5% (w/v) glucose, ▲: 1% (w/v) NaB, ■: 1% (w/v) FOS, ●: 1% (w/v) B-FOS, ◆: 1% (w/v) glucose, x: distilled water (sterile DI water)).

As a result of tests, glucose contained as a positive control group was used for all bacteria used for tests. A basal medium not containing a carbon source was used as a negative control group and most bacteria cultured in a medium containing the negative control group and NaB could not be grown well, as compared to the positive control group. In particular, regarding the negative control group, *Staphylococcus aureus* ($OD_{600}$=0.36) and *Clostridium butyricum* ($OD_{600}$=0.49), which belong to non-probiotic strains had maximum $OD_{600}$ of 0.25 and 0.42, respectively, in the presence of 1% (w/v) NaB, which means that the growth of bacteria was significantly inhibited.

The growth of Bifidobacteria used for the test was facilitated due to addition of glucose as a positive control group and of FOS well-known as a conventional prebiotic. Meanwhile, B-FOS significantly facilitated the growth of *Bifidobacterium bifidum* BGN4, *Bifidobacterium longum* BORI, *Bifidobacterium catenulatum*, *Bifidobacterium animalis* (*B. animalis*) and *Bifidobacterium adolesentis* (*B. adolesentis*) (FIGS. 6 to 7).

In addition, B-FOS significantly contributed to the growth of *Lactobacillus casei*, *Lactococcus lactis* and *Streptococcus thermophilus* and also contributed to the growth of other subject lactic acid bacteria to some extent (FIG. 8).

Meanwhile, FOS significantly facilitated the growth of most non-probiotic strains, excluding *Staphylococcus aureus* (*S. aureus*) and *Enterococcus faecalis* (*E. faecalis*). On the other hand, as compared to the negative control group, B-FOS did not contribute to the growth of most non-probiotic bacteria, excluding *Listeria monocytogenes*, *Clostridium perfringens*, and *Bacteroides thetaiotaomicron*.

Consequently, B-FOS was a prebiotic material which facilitated the growth of *Bifidobacterium*, while not having an influence on use of non-probiotic bacteria (FIGS. 9 to 10).

Test Example 2: B-FOS Use and Degradation of Intestinal Bacteria (1) Analysis of Bacterial Culture Supernatant Depending on the Type of Carbon Source of Medium The culture solutions of *Bifidobacterium longum* BORI and *Enterococcus faecalis* (*E. faecalis*) were analyzed by thin layer chromatography and the carbon sources consumed by bacteria were thus compared. TLC conditions were the same as conditions used for B-FOS purification. In addition, for analysis of metabolites, the culture supernatants of *Bifidobacterium longum* BORI, *Enterococcus faecalis* (*E. faecalis*), *Bifidobacterium bifidum* BGN4, *Lactobacillus casei*, *Bifidobacterium catenulatum*, *Escherichia coli* (*E. coli*), and *Bifidobacterium longum* (*B. longum*) RD47 were analyzed by high-performance liquid chromatography (HPLC).

To analyze whether or not intestinal bacteria consumed B-FOS by degradation and fermentation as an energy source, whether or not lactic acid, acetic acid or butyric acid was produced was checked. Exterior standard materials were analyzed under the same conditions as samples and a calibration curve thereof was drawn at four different concentrations. The control group was a bacterium-free medium. A YL9100 HPLC system (Younglin, Anyang, South Korea) was used, and an Aminex HPX-87H column and a 300×7.8 mm column (Bio-rad, California, USA) were used. The mobile phase used herein was 5 mM sulfuric acid, a flow rate was 0.6 ml/min, and a column temperature was maintained at 50° C. All of the culture solutions were filtered through a PVDF Acrodisc syringe filter (0.2 μm, 13 mm, Pall Corporation, Michigan, USA) and were injected in an amount of 20 μl. All HPLC analyses of the following tests were conducted under these conditions. Table 2 shows HPLC analysis conditions of lactic acid, acetic acid and butyric acid.

TABLE 2

| Instrument | YL9100 HPLC system |
| --- | --- |
| Column | Aminex HPX-87H column |
| | 300 × 7.8 mm |
| Mobile phase | 5 mM $H_2SO_4$ |
| Flow rate | 0.6 mL/min |
| Temperature | 50° C. |
| Detection | Refractive Index(RI) |
| Injection volume | 20 μl |

TLC results of culture supernatants of *Bifidobacterium longum* BORI and *Enterococcus faecalis* (*E. faecalis*) cultured in media each containing FOS, B-FOS and glucose as carbon sources showed that, when culturing in a medium containing bacteria, bands of FOS, B-FOS and glucose as carbon sources disappeared or became weaker, as compared to when culturing in a medium containing no bacteria (FIG. 11). FIG. 11 shows TLC results of culture supernatants of *Bifidobacterium longum* BORI and *Enterococcus faecalis* (*E. faecalis*).

B-FOS exhibited weaker intensity of bands when culturing *Bifidobacterium longum* BORI, as compared to when culturing *Enterococcus faecalis* (*E. faecalis*). Lactic acid, acetic acid and butyric acid present in culture supernatants of four bacteria of *Bifidobacterium longum* BORI, *Bifidobacterium bifidum* BGN4, *Lactobacillus casei*, and *Bifidobacterium catenulatum*, which underwent facilitation of growth in a B-FOS medium by containing *Bifidobacterium longum*) BORI, and in culture supernatants of three bacteria of *Escherichia coli* (*E. coli*), *Bifidobacterium longum* (*B. longum*) RD47, and *Enterococcus faecalis* (*E. faecalis*), which did not undergo facilitation of growth, were identified by high-performance liquid chromatography and results are shown in Table 3.

TABLE 3

| | Control | | | Nab | | | FOS | | | B-Fos | | | Glucose | | |
| --- | --- | --- | --- | --- | --- | --- | --- | --- | --- | --- | --- | --- | --- | --- | --- |
| | Lactic acid | Acetic acid | Butyric acid | Lactic acid | Acetic acid | Butyric acid | Lactic acid | Acetic acid | Butyric acid | Lactic acid | Acetic acid | Butyric acid | Lactic acid | Acetic acid | Butyric acid |
| PBS | + | + | − | + | + | +++ | ++ | ++ | − | + | + | − | + | + | − |
| B. bifidum BGN4 | ++ | + | − | + | + | +++ | +++ | ++ | − | +++ | + | + | +++ | + | − |
| B. longum BORI | + | + | − | + | + | +++ | ++ | ++ | − | + | ++ | + | +++ | ++ | − |
| B. catenulatum | + | + | − | ++ | + | +++ | ++ | ++ | − | ++ | ++ | + | ++ | ++ | − |
| B. longum RD47 | + | + | − | + | + | +++ | +++ | ++ | − | + | + | − | +++ | + | − |
| L. casei | ++ | + | − | + | + | +++ | +++ | ++ | − | +++ | ++ | + | +++ | + | − |
| Bac. Thetaiotaomicron | − | ++ | − | − | + | +++ | ++ | + | − | ++ | + | + | ++ | ++ | − |
| E. coli | − | ++ | − | − | + | +++ | ++ | ++ | − | + | + | − | +++ | ++ | − |
| E. Faecalis | + | + | − | + | + | +++ | +++ | + | − | + | + | + | +++ | + | − |
| Bac. Fragilis | + | + | − | + | + | +++ | +++ | + | − | + | + | + | +++ | + | − |

The number of '+' represents the concentration of organic acid.
'−'; not detected,
'+'; 0.05% (v/v) or less,
'++' 0.05% (v/v) – 0.25% (v/v),
'+++'; no more than 0.25% (v/v)

Butyric acid was detected from culture solutions of all strains cultured in NaB, but great amounts of acetic acid and lactic acid were detected from all strains cultured in a medium containing FOS and glucose, and the amount of lactic acid was greater than that of acetic acid. Regarding the B-FOS medium, butyric acid, which was not detected in a medium containing FOS and glucose, was detected from culture supernatants of all strains excluding *Escherichia coli*

(*E. coli*) and *Bifidobacterium longum* (*B. longum*) RD47. In particular, bacteria using B-FOS such as *Bifidobacterium bifidum* BGN4, *Lactobacillus casei* and *Bifidobacterium catenulatum*, which underwent facilitation of growth by B-FOS, could be used for energy production and bacterial growth by metabolizing, degrading and fermenting B-FOS.

(2) Reaction of B-FOS with Bacterial Culture Supernatant (Culture Supernatant), Bacteria (Cell Suspension) and Bacterial Fragmented Solution (Cell Extract)

Strains used to further identify whether or not B-FOS was hydrolyzed by bacteria were *Bifidobacterium bifidum* BGN4, *Lactobacillus casei*, and *Enterococcus faecalis* (*E. faecalis*). The bacterial suspensions were centrifuged to isolate the bacteria from the culture liquid. The bacteria were washed with PBS twice and then a suspension of the bacteria in PBS was used. The bacterial fragmented solution (cell extract) was obtained by crushing the suspension in PBS with an ultrasonicator (Qsonica, Newtown, Conn. USA) every five minutes (amp 38%) for 10 minutes, centrifuging (15,000×g, 10 min) the same and isolating the supernatant as the bacterial fragmented solution. The control group was a group containing no bacterium. 120 µl of the bacterial culture solution (cell suspension), the bacterial suspension (cell suspension) and the bacterial fragmented solution (cell extract) were each reacted at 37° C. with 20 µl of 10% (w/v) B-FOS and FOS solutions for 1 hour and the reaction solution was heated with boiling water for 10 minutes to cease reaction. Results before and after the reaction were compared by TLC, and whether or not butyric acid was degraded was analyzed by HPLC.

The cell suspension, cell extract and culture supernatant of *Bifidobacterium bifidum* BGN4, *Lactobacillus casei* and *Enterococcus faecalis* (*E. faecalis*) were each reacted with FOS and B-FOS, and whether or not B-FOS was degraded by bacteria was identified by TLC (FIG. 12). FIG. 12 shows results of TLC analysis of the cell suspension, culture supernatant and cell extract before (A) and after (B) reaction with FOS and B-FOS.

Test results showed FOS had no change in TLC before and after reaction in all reactions. Meanwhile, when the bacteria (cell suspension) and the bacterial fragmented solution (cell extract) reacted with B-FOS, as compared to before the reaction, all bands of FOS in three strains were created and bands were not observed upon reaction with the bacterial culture supernatant. Analysis results of detection of butyric acid through HPLC are shown in Table 4.

TABLE 4

|  | B.bifidum BGN4 | | L.casei | | E.faecalis | |
|---|---|---|---|---|---|---|
|  | B-FOS | DI water | B-FOS | DI water | B-FOS | DI water |
| Cell suspension | + | − | + | − | + | − |
| Culture supernatant | − | − | − | − | − | − |
| Cell extract | + | − | + | − | + | − |

'+'; Butyric acid was detected,
'−'; Butyric acid was not detected

Regarding all three strains, when the bacteria (cell suspension) and bacterial fragmented solution (cell extract) reacted with B-FOS, butyric acid was detected, but, when the bacterial culture supernatant (culture supernatant) reacted with B-FOS, butyric acid was not detected. In addition, such a reaction occurred in all analyzed bacteria. Accordingly, the factor of hydrolysis of B-FOS was considered to be present on the wall of bacterial cells or in the bacterial cells. As a result, FOS and butyric acid produced from B-FOS could be considered to affect the growth of bacteria.

Test Example 3: Effects of B-FOS on Proliferation of Enterocytes (1) Change in Growth of Caco-2 Cells Depending on Medium Composition To avoid main use of glucose as an energy source for cell growth in a standard culture medium of Caco-2 cells containing a high concentration of glucose (4.5 g/L), cellular growth was compared in the presence of a high concentration of glucose (4.5 g/L) and pyruvate using a glucose-free DMEM (Dulbecco's modified Eagle's medium; Gibco BRL, Grand Island, N.Y., USA).

10% (w/v) solutions of NaB, FOS and B-FOS in PBS were prepared and filtered through a 0.2 µm membrane filter. NaB, FOS and B-FOS were each prepared at a concentration of 0.005 to 0.06% (w/v) in a DMEM medium containing high concentrations of glucose (4.5 g/L) and pyruvate (Glu+Pyr+) and a DMEM medium not containing the same (Glu−Pyr−), and were then used for the test.

$5 \times 10^5$ cells were seeded in a dose of 1.5 mL in a 25 $cm^2$ flask (SPL Life Science, Pocheon, South Korea) and cultured for 3 days in 37° C., 5% $CO_2$ cell incubator until 50% confluence was obtained. Then, the medium was replaced with a medium supplemented with 0.005 to 0.06% (w/v) of NaB, FOS and B-FOS and then cultured under the same conditions for 4 days. The culture supernatant was harvested for testing and adsorbed cells were washed with PBS twice, were treated with trypsin/EDTA, and were isolated from the flask. The isolated cells were dyed with a 0.4% trypan blue solution, and the number of living cells was counted with a hematocytometer (Marienfeld-Superior, Berlin, Germany). The control group was a medium supplemented with PBS and a mean of values obtained by repeating tests three times is shown.

Test results showed that, when NaB was added to the medium (Glu+Pyr+) containing high concentrations of glucose (4.5 g/L) and pyruvate, at concentrations of 0.005%, 0.04% and 0.06% (w/v), the number of cells was decreased in about 30%, 50% and 65%, as compared to the control group (FIG. 13A). Meanwhile, in the medium not containing glucose and pyruvate (Glu−Pyr−), the number of cells was increased at 0.005% and 0.02% (w/v), but there was no significant difference between the medium and the control group at 0.04% (w/v). However, at a concentration of 0.06% (w/v), this medium exhibited a 35% decrease in the number of cells, as compared to the control group (FIG. 13B). Regarding FOS-containing media, there was no significant difference between Glu+Pyr+ medium and Glu−Pyr− medium (FIGS. 13C and 13D). When B-FOS was added, both Glu+Pyr+ medium and Glu−Pyr− medium did not show a significant difference from the control group at 0.02% (w/v), but showed a significant increase of about 1.5- and 1.7-fold in the number of cells at a concentration of 0.06% (w/v) (FIGS. 13E and 13F). FIG. 13 shows the number of cells measured at different concentrations of substances after adding NaB, FOS and B-FOS at a concentration of 0 to 0.06% (w/v) depending on presence of glucose and pyruvate, and culturing for 4 days (A: Glu+Pyr+NaB+, B: Glu−Pyr−NaB+, C: Glu+Pyr+FOS+, D: Glu−Pyr−FOS+, E: Glu+Pyr+B−FOS+, F: Glu−Pyr−B−FOS+).

This means that B-FOS is used as an energy source of Caco-cells to facilitate proliferation of intestinal epithelial cells.

(2) B-FOS Use and Degradation of Caco-2 Cells.

In order to identify whether or not Caco-2 cells used B-FOS depending on an alternative energy source, the harvested Caco-2 cell culture solution was analyzed by TLC to identify a consumed carbon source and whether or not butyric acid was present was identified by HPLC (FIG. 14). FIG. 14 shows results of TLC analysis of the culture supernatant after culturing Caco-2 cells in a medium containing FOS and B-FOS.

Test results showed that glucose bands present in the Glu+Pyr+ medium completely disappeared in all media after culture, but FOS had no change in TLC in both Glu+Pyr+ medium and Glu−Pyr− medium. Culture supernatants of Glu+Pyr+ medium and Glu−Pyr− medium containing B-FOS showed creation of FOS bands and Glu−Pyr− medium exhibited more remarkable bands than the Glu+Pyr+ medium. Some B-FOS bands disappeared in Glu−Pyr− medium. Accordingly, B-FOS was used by Caco-2 cells and, as a result, FOS was produced. As a result of identification of presence of butyric acid in the cell culture solution and cell fragmented solution (cell extract) harvested after culture, butyric acid was not detected in both. This is considered that butyric acid degraded during culture was used by cells.

The culture supernatant of Caco-2 cells cultured in a general medium was used as a cell culture solution to identify whether B-FOS was degraded by Caco-2 cells. The cell suspension used herein was obtained by treating cells with trypsin/EDTA, isolating the same, washing the resulting cells with PBS twice and preparing a suspension of the cells in PBS, and the cell fragmented solution (cell extract) was obtained by crushing the suspension using an ultrasonic crusher every four minutes (amp 25%) for 8 minutes, centrifuging the suspension and preparing the resulting supernatant as the cell fragmented solution (cell extract). 450 µl of the cell culture solution (culture supernatant), cell suspension and cell fragmented solution (cell extract) were reacted with 50 µl of 10% (w/v) FOS and B-FOS for 3 hours at 37° C. Degradation (lysis) was analyzed by comparing before and after reaction through TLC and degradation of butyric acid from B-FOS was analyzed by HPLC (FIG. 15). FIG. 15 shows TLC analysis after reacting the culture supernatant, cell suspension and cell extract of Caco-2 cells with FOS and B-FOS.

Test results showed that FOS underwent no phase change in TLC between before and after reaction in all reactions. Meanwhile, all of the culture supernatant, cell suspension and cell extract, which had reacted with B-FOS, showed creation of FOS bands. The results of analysis to identify the degradation of butyric acid from B-FOS through HPLC showed that a small amount of butyric acid was detected from the culture supernatant, cell suspension and cell extract reacted with B-FOS.

(3) Measurement of Cell Viability by MTT(3-(4,5-Dimethylthiazol-2-Yl) 2,5-Diphenyltetrazolium Bromide) Analysis MTT analysis was conducted to confirm cytotoxicity derived from B-FOS. 100 µl of Caco-2 cells were seeded at a density of 2,000 cells/well onto a 96-well plate and cultured at 37° C. in a 5% $CO_2$ cell incubator for 48 hours. Then, the present medium was removed and replaced with 180 µl of a medium supplemented with 0.02 to 0.1% (w/v) of NaB, FOS and B-FOS for 24 hours, 48 hours and 72 hours. After completion of culture, 20 µl of a 5 mg/mL MTT solution was added to each well, reaction was conducted for 4 hours again and the supernatant was removed. The formed crystal was dissolved in 100 µl of dimethyl sulfoxide (DMSO) and an absorbance at 750 nm was measured using a microplate spectrophotometer. Cell viability was represented as a percentage with respect to the control group with no treatment and a mean of values by repeating the test four times was indicated (FIG. 16). FIG. 16 shows results of cytotoxicity confirmed by MTT analysis to confirm effects of NaB, FOS and B-FOS on cell viability of Caco-2 cells.

Test results showed that NaB exhibited a significant decrease in cell viability to 81±15% at a concentration of 0.1% (w/v) after 48 hours. In addition, cell viability was significantly decreased to 45±6.9% at 0.1% (w/v) after 72 hours. On the other hand, FOS and B-FOS did not show a significant difference from the control group at all concentrations for 72 hours and had no cytotoxicity up to 0.1% (w/v).

Test Example 4: Acute Toxicity Test of B-FOS Upon Oral Administration of ICR to Mice For the acute toxicity test of B-FOS, 40 mice in total were divided into eight groups. The mice were acclimated for one week after caging and were fasted for 3 to 4 hours before oral administration of B-FOS, and for 1 to 2 hours after oral administration. B-FOS was administered only once and the mice were observed for 14 days after administration. Substances each fed to the eight groups are given below.

First group: control group (five female mice); second group: control group (five male mice); third group: 500 mg/kg B-FOS oral administration (five female mice); fourth group: 500 mg/kg B-FOS oral administration (five male mice); fifth group: 1,000 mg/kg B-FOS oral administration (five female mice); sixth group: 1,000 mg/kg B-FOS oral administration (five male mice); seventh group: 2,000 mg/kg B-FOS oral administration (five female mice); eighth group: 2,000 mg/kg B-FOS oral administration (five male mice). After 3 weeks, the test end day, euthanasia was induced by carbon dioxide hyperventilation and the mice were then dissected. Mouse weight, and coefficients of liver, kidney and spleen were measured, blood chemistry analysis and tissue analysis were conducted, and respective weights are shown in Table 5.

TABLE 5

| Groups | Body weight (g) | | Liver | Spleen | Kidney |
| | Before | After | (mg/g) | (mg/g) | (mg/g) |
| --- | --- | --- | --- | --- | --- |
| Male | | | | | |
| Control | 35.04 ± 4.17 | 41.06 ± 6.55 | 41.06 ± 9.51 | 3.84 ± 1.02 | 7.18 ± 1.54 |
| 500 mg/kg | 34.80 ± 0.67 | 39.58 ± 2.32 | 39.58 ± 7.09 | 3.57 ± 1.48 | 7.55 ± 1.55 |

TABLE 5-continued

| Groups | Body weight (g) Before | Body weight (g) After | Liver (mg/g) | Spleen (mg/g) | Kidney (mg/g) |
|---|---|---|---|---|---|
| 1000 mg/kg | 34.04 ± 1.25 | 38.72 ± 1.61 | 38.72 ± 5.12 | 4.66 ± 1.20 | 7.76 ± 0.33 |
| 2000 mg/kg | 36.28 ± 4.65 | 42.14 ± 5.98 | 42.14 ± 4.13 | 4.25 ± 0.90 | 7.52 ± 1.32 |
| Female | | | | | |
| Control | 27.96 ± 1.47 | 31.56 ± 0.79 | 45.67 ± 3.34 | 3.79 ± 1.33 | 7.59 ± 1.66 |
| 500 mg/kg | 27.86 ± 2.67 | 32.18 ± 3.00 | 47.90 ± 2.53 | 4.32 ± 1.52 | 6.86 ± 1.30 |
| 1000 mg/kg | 26.94 ± 1.78 | 30.20 ± 1.48 | 47.07 ± 4.54 | 4.00 ± 1.60 | 6.65 ± 2.46 |
| 2000 mg/kg | 26.60 ± 1.76 | 30.82 ± 1.65 | 46.34 ± 7.89 | 3.91 ± 1.48 | 7.16 ± 1.52 |

Measurement results showed that there was no significant difference in body weight between male groups or female groups. In addition, there was no significant difference in coefficients of liver, kidney and spleen between male groups or female groups. The increase in these coefficients means that inflammation may be induced.

The functional change index of body relating to presence of inflammation or disease may be evaluated by a biochemical indicator of blood serum. Accordingly, in the present test, a biochemical indicator in blood serum of female and male mice is shown after exposure of 0, 500, 1000 and 2,000 mg/kg to B-FOS (FIG. 17). FIG. 17 shows biochemical indicators in blood serum of female and male mice after exposure to B-FOS. After oral administration, a significant change in albumin, TBIL and AST and ALP enzymes (p>0.05) was not detected. This parameter relates to liver function. Kidney toxicity can be seen from BUN and Cr. No increase in Bun and Cr means the absence of kidney damage. Cellular membrane damage and tissue damage were evaluated by LDH and a significant change in LDH in the female or male group was not observed.

As can be seen from FIGS. 18 to 24, the histopathologic analysis results of heart, liver, kidney, lung, spleen, stomach, testicle and ovary tissues showed that there were no abnormal pathological changes in tissues. FIG. 18 shows heart tissue dyeing results of ICR mice to which B-FOS is administered, FIG. 19 shows kidney tissue dyeing results of ICR mice to which B-FOS is administered, FIG. 20 shows liver tissue dyeing results of ICR mice to which B-FOS is administered, FIG. 21 shows lung tissue dyeing results of ICR mice to which B-FOS is administered, FIG. 22 shows spleen tissue dyeing results of ICR mice to which B-FOS is administered, FIG. 23 shows stomach tissue dyeing results of ICR mice to which B-FOS is administered and FIG. 24 shows testicle and ovary tissue dyeing results of ICR mice to which B-FOS is administered ((A) to (D): male mouse, (E) to (H): female mouse, and control group, 500 mg/kg, 1000 mg/kg and 2000 mg/kg in this order from the left).

Test Example 5: Effects of B-FOS on Contents of Short Chain Fatty Acid in Fecal Bacteria and in the Caecum of ICR Mouse In order to identify effects of B-FOS on contents of short chain fatty acid in fecal bacteria and in the caecum of ICR mice, 16 mice in total were divided into two groups for testing. The mice were acclimated for one week after caging, and at 2 weeks, a diet was fed to each group for one week and feces were collected. This process was conducted over four weeks in total. The subject animals were observed at least daily to check dietary intake and monitor animal conditions. Substances each fed to the eight groups are given below:

First group: general diet; Second group: general diet and 0.5% B-FOS.

In order to analyze short chain fatty acid in faces of the mouse caecum, an YL9100 HPLC system (Younglin, Anyang, South Korea), an Aminex HPX-87H column and a 300×7.8 mm column (Bio-rad, California, USA) were used. The mobile phase used herein was 5 mM sulfuric acid, the flow rate was 0.6 mL/min, and the column temperature was maintained at 50° C. All culture solutions were filtered through a PVDF Acrodisc syringe filter (0.2 μm, 13 mm, Pall Corporation, Michigan, USA) and were administered in an amount of 20 μl. Results are shown in Table 6.

TABLE 6

| | Lactic acid (mM) | Acetic acid (mM) | Butyrate (mM) |
|---|---|---|---|
| Control | 4.39 ± 0.80 | 4.33 ± 1.61 | 0 |
| B-FOS | 5.66 ± 2.45 | 6.30 ± 2.84 | 18.36 ± 2.99 |

Test results showed that, as compared to the B-FOS-free general diet group (control), the B-FOS test group exhibited a higher concentration of short chain fatty acid. All of lactic acid, acetic acid and butyrate were increased and, in particular, butyrate was detected at a considerably high concentration of 18.36±2.99 mM, in the B-FOS test group, as compared to the control group.

As is apparent from the above description, the butyryl-fructooligosaccharides (B-FOS) according to the present invention are prebiotics which facilitate selective growth of probiotics, thereby controlling intestinal microbes and contributing to physiological functions as an energy source of intestinal epithelial cells.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A prebiotic composition comprising a butyryl-fructooligosaccharide(s) (B-FOS) as a sole active ingredient, wherein the B-FOS is composed of 2 to 5 fructose units linked to a glucose unit, and 1 to 2 butyryl groups linked to OH groups of the fructose or glucose units via esterification, and the B-FOS controls an intestinal bacteria by selectively increasing growth of a probiotic while not affecting growth of a non-probiotic which is a pathogenic bacteria selected from the group consisting of *Staphylococcus aureus, Escherichia coli, Enterococcus faecalis, Prevotella intermedia* and *Clostridium ramosum*, wherein the probiotic is *Bifidobacterium*.

2. The prebiotic composition according to claim 1, wherein the *Bifidobacterium* comprises any one selected from the group consisting of *Bifidobacterium bifidum, Bifidobacterium longum, Bifidobacterium catenulatum* and *Bifidobacterium animalis*.

\* \* \* \* \*